US008779092B2

(12) United States Patent
Bussolino et al.

(10) Patent No.: US 8,779,092 B2
(45) Date of Patent: Jul. 15, 2014

(54) METASTASIS-SPECIFIC PEPTIDES AND THEIR DIAGNOSTIC AND THERAPEUTIC APPLICATIONS

(75) Inventors: Federico Bussolino, Turin (IT); Serena Marchio, Turin (IT)

(73) Assignee: Universita Degli Studi di Torino, Turin (IT)

( * ) Notice: Subject to any disclaimer, the term of this patent is extended or adjusted under 35 U.S.C. 154(b) by 1214 days.

(21) Appl. No.: 12/516,896

(22) PCT Filed: Nov. 30, 2007

(86) PCT No.: PCT/EP2007/010428
§ 371 (c)(1),
(2), (4) Date: May 29, 2009

(87) PCT Pub. No.: WO2008/064910
PCT Pub. Date: Jun. 5, 2008

(65) Prior Publication Data
US 2010/0041614 A1   Feb. 18, 2010
US 2010/0210563 A2   Aug. 19, 2010
US 2011/0294743 A9   Dec. 1, 2011

(30) Foreign Application Priority Data
Nov. 30, 2006 (IT) .............................. TO2006A0852

(51) Int. Cl.
*C07K 11/00* (2006.01)
(52) U.S. Cl.
USPC ....... 530/329; 530/388.8; 514/21.7; 514/19.3
(58) Field of Classification Search
None
See application file for complete search history.

(56) References Cited

U.S. PATENT DOCUMENTS

| 6,551,795 | B1 * | 4/2003 | Rubenfield et al. | 435/69.1 |
| 6,703,491 | B1 * | 3/2004 | Homburger et al. | 536/23.1 |
| 7,709,624 | B2 * | 5/2010 | Nakashima et al. | 536/24.1 |
| 2004/0172684 | A1 * | 9/2004 | Kavalic et al. | 435/69 |

FOREIGN PATENT DOCUMENTS

| WO | 03/086284 A | 10/2003 |
| WO | WO03/086284 A2 * | 10/2003 |
| WO | WO 2004093804 A2 * | 11/2004 |
| WO | WO 2006069610 A2 * | 7/2006 |
| WO | WO 2007104062 A2 * | 9/2007 |
| WO | WO 2007131300 A1 * | 11/2007 |

OTHER PUBLICATIONS

Nakashima and Tamura Recombinant Proteins Over a Wide temperature Range From 4 to 35° C., Biotechnology and Bioengineering vol. 86, Issue 2, Feb. 19, 2004.*
Pall Corporation, Protein Purification and Handling; http://www.pall.com/main/Laboratory/Literature-Library-Details.page?id=35497; last visited Sep. 26, 2012.*
Makino et. al. Genome sequence of *Vibrio parahaemolyticus*: a pathogenicmechanism distinct from that of *V cholerae*, Mechanisms of Disease, The Lancet • vol. 361 • Mar. 1, 2003 • www.thelancet.com (provided for consideration).*
Makino et. al. Genome Sequence of *Vibrio parahaemolyticus*: a pathogenic mechanism distinct from that of *V. Cholorae*, Lancet 361: 743-749, 2003.*
Brown C K et al: "A novel approach for the identification of unique tumor vasculature binding peptides using an *E. coli* peptide display library" Annals of Surgical Oncology, vol . 7, No. 10, Dec. 2000, pp. 743-749.
Rasmussen UB et al: "Tumor cell-targeting by phage-display peptides" Cancer Gene Therapy, vol. 9, Jan. 1, 2002, pp. 606-612.
Kelly KA et al: "Isolation of a colon tumor specific binding peptide using peptide phage display selection"Sep. 1, 2003, vol. 5, No. 5, Sep. 1, 2003, pp. 437-444.
Li Xiao-Bo et al: "Molecular addresses of tumors: selection by in vivo phage display" Archivum Immunologiae Et Therapiae Experimentalis, May-Jun. 2006, vol. 54, No. 3, May 2006, pp. 177-181.
Tang Zhao-You et al: "A decade's studies on metastasis of hepatocellular carcinoma" Journal of Cancer Research and Clinical Oncology Apr. 2004, vol. 130, No. 4, Apr. 2004, pp. 187-196.
Gui J et al: "Selection of a peptide with affinity for the tumor-associated TAG72 antigen from a phage-displayed library", Biochemical and Biophysical Research Communications, vol. 218, Jan. 1, 1996, pp. 414-419.
Maruta F et al: "Identification of FGF receptor-binding peptides for cancer gene therapy" Cancer Gene , Therapy, vol. 9, Jan. 1, 2002, pp. 543-552.
Trepel Martin et al: "In vivo phage display and vascular heterogeneity: implications for targeted medicine." Current Opinion in Chemical Biology, 2002, vol. 6, No. 3, Jun. 2002, pp. 399-404.
Du et al: "In vitro panning of a targeting peptide to hepatocarcinoma from a phage display peptide library" Biochemical and Biophysical Research Communications, vol. 342. No. 3, Apr. 14, 2006, pp. 956-962.
Lin et al., "Genome wide expression profiling identifies genes associated with colorectal liver metastasis", Oncology Reports, 17: 1541-1549, 2007.
Habermann et al., "Stage-Specific Alterations of the Genome, Transcriptome, and Proteome During Colorectal Carcinogenesis", Genes, Chromosomes & Cancer, 46:10-26 (2007).
Brown C K et al: "A novel approach for the identification of unique tumor vasculature binding peptides using an *E. coli* peptide display library" Annals of Surgical Oncology, vol. 7, No. 10, Dec. 2000, pp. 743-749.
Kelly KA et al: "Isolation of a colon tumor specific binding peptide using peptide phage display selection", vol. 5, No. 5, Sep. 1, 2003, pp. 437-444.
Maruta F et al: "Identification of FGF receptor-binding peptides for cancer gene therapy" Cancer Gene Therapy, vol. 9, Jan. 1, 2002, pp. 543-552.
Hu et al., "Phage Display Selection of Peptides that Inhibit Metastasis Ability of Gastric Cancer Cells with High Liver-Metastatic Potential", Biochemical and Biophysical Research Communications, vol. 341, No. 3, pp. 964-972, 2006.

* cited by examiner

*Primary Examiner* — Christina Bradley
*Assistant Examiner* — Jeanette Lieb
(74) *Attorney, Agent, or Firm* — Rothwell, Figg, Ernst & Manbeck, P.C.

(57) ABSTRACT

The present invention concerns peptide sequences that specifically recognize cells of human hepatic metastases. The invention comprises also the use of nucleic acids coding for such peptides, as well as conjugates and formulations of such peptides for diagnostic and therapeutic purposes.

32 Claims, 6 Drawing Sheets

Figure 1

| | |
|---|---|
| ARPGLRS | SEQ ID NO. 1 |
| MRYALRS | SEQ ID NO. 2 |
| LRPGLRS | SEQ ID NO. 3 |
| LRSGSGS | SEQ ID NO. 4 |
| VRSGRGS | SEQ ID NO. 5 |
| GIYRLRS | SEQ ID NO. 6 |
| GVYSLRS | SEQ ID NO. 7 |
| KYPFDKL | SEQ ID NO. 8 |
| KVYESWS | SEQ ID NO. 9 |
| GLDTLLV | SEQ ID NO. 10 |
| QSRMLRI | SEQ ID NO. 11 |
| AAFLQGG | SEQ ID NO. 12 |
| RSYFEML | SEQ ID NO. 13 |
| YLHLLPP | SEQ ID NO. 14 |
| RPTLITP | SEQ ID NO. 15 |
| ASRVRLP | SEQ ID NO. 16 |
| MYVVHAD | SEQ ID NO. 17 |
| GPTLIKL | SEQ ID NO. 18 |
| APALYHV | SEQ ID NO. 19 |
| SVDSQMG | SEQ ID NO. 20 |
| VVSMVGV | SEQ ID NO. 21 |
| HLLAVSY | SEQ ID NO. 22 |
| PGCALGS | SEQ ID NO. 23 |
| AAGEWSG | SEQ ID NO. 24 |
| PRLGHGS | SEQ ID NO. 25 |
| RAGGGRL | SEQ ID NO. 26 |
| LTVRAVD | SEQ ID NO. 27 |
| PLGWLSY | SEQ ID NO. 28 |
| CHRTMRN | SEQ ID NO. 29 |
| LRGGIGV | SEQ ID NO. 30 |
| FFDGAGS | SEQ ID NO. 31 |
| RRIDDFR | SEQ ID NO. 32 |
| HLSLAGL | SEQ ID NO. 33 |
| RPRTDTY | SEQ ID NO. 34 |
| FSQGKLA | SEQ ID NO. 35 |
| TMETGGS | SEQ ID NO. 36 |
| GVRSVRN | SEQ ID NO. 37 |
| HSQRFGK | SEQ ID NO. 38 |
| VSALELS | SEQ ID NO. 39 |
| AGMVLWT | SEQ ID NO. 40 |
| PDGRFGG | SEQ ID NO. 41 |

Figure 1 (cont.)

| | |
|---|---|
| ESPSRHT | SEQ ID NO. 42 |
| ARGFPGV | SEQ ID NO. 43 |
| QSSSVIL | SEQ ID NO. 44 |
| RWTSSRS | SEQ ID NO. 45 |
| AYTNFVY | SEQ ID NO. 46 |
| SVLENAI | SEQ ID NO. 47 |
| LVGNFGL | SEQ ID NO. 48 |
| GLVGSRV | SEQ ID NO. 49 |
| RTFSKLG | SEQ ID NO. 50 |
| GSIVMLS | SEQ ID NO. 51 |
| AGGGLLR | SEQ ID NO. 52 |
| GVRLLTA | SEQ ID NO. 53 |
| WGAEWSS | SEQ ID NO. 54 |
| VREDKGI | SEQ ID NO. 55 |
| LFILVSG | SEQ ID NO. 56 |
| ASWTARV | SEQ ID NO. 57 |
| GRFMGAF | SEQ ID NO. 58 |
| NRTRFSS | SEQ ID NO. 59 |
| VLGIAVS | SEQ ID NO. 60 |
| ELAQAIS | SEQ ID NO. 61 |
| KSVGGLQ | SEQ ID NO. 62 |
| TCSRLLT | SEQ ID NO. 63 |
| FCLLCHM | SEQ ID NO. 64 |
| NRGRGYL | SEQ ID NO. 65 |
| FFWSTAQ | SEQ ID NO. 66 |
| FLFWGRT | SEQ ID NO. 67 |
| VMLSTGP | SEQ ID NO. 68 |
| GIVCLGR | SEQ ID NO. 69 |
| GVHSRCG | SEQ ID NO. 70 |
| YRGFPPP | SEQ ID NO. 71 |
| ARGMPLF | SEQ ID NO. 72 |
| CRDSCGR | SEQ ID NO. 73 |
| GLLCGRD | SEQ ID NO. 74 |
| IRVSYGR | SEQ ID NO. 75 |
| WRRVGDL | SEQ ID NO. 76 |
| LGSGSWP | SEQ ID NO. 77 |
| VFSPVNP | SEQ ID NO. 78 |
| SLQSVVA | SEQ ID NO. 79 |
| IRGIGGA | SEQ ID NO. 80 |
| KVFARLG | SEQ ID NO. 81 |
| VGRTVIQ | SEQ ID NO. 82 |
| GLPRLSG | SEQ ID NO. 83 |
| DCVWDCM | SEQ ID NO. 84 |

Figure 1 (cont.)

| | |
|---|---|
| GLGIYVL | SEQ ID NO. 85 |
| FFITPRS | SEQ ID NO. 86 |
| MGGSLFG | SEQ ID NO. 87 |
| AARYGID | SEQ ID NO. 88 |
| WRRSERT | SEQ ID NO. 89 |
| KLSGVSL | SEQ ID NO. 90 |
| WVGGIRG | SEQ ID NO. 91 |
| IPRSTFG | SEQ ID NO. 92 |
| VCWASWC | SEQ ID NO. 93 |
| VRASPSL | SEQ ID NO. 94 |
| PLLYRNA | SEQ ID NO. 95 |
| LRSGRGS | SEQ ID NO. 96 |
| WALTTAL | SEQ ID NO. 97 |
| IVFGRGS | SEQ ID NO. 98 |
| MRVFGGV | SEQ ID NO. 99 |
| VLGSLGS | SEQ ID NO. 100 |
| LWSEPMV | SEQ ID NO. 101 |
| ERAPLKA | SEQ ID NO. 102 |
| ISRFGYV | SEQ ID NO. 103 |
| GLKFNWS | SEQ ID NO. 104 |
| KSSEIPR | SEQ ID NO. 105 |
| RRALFAT | SEQ ID NO. 106 |
| GWRGLRT | SEQ ID NO. 107 |
| DYFWFAD | SEQ ID NO. 108 |
| SRYWTRS | SEQ ID NO. 109 |
| RREGLRS | SEQ ID NO. 110 |
| SWYTLRS | SEQ ID NO. 111 |
| VSMSRSL | SEQ ID NO. 112 |
| LAYRLRS | SEQ ID NO. 113 |
| VYYGLRR | SEQ ID NO. 114 |
| LTYRLRS | SEQ ID NO. 115 |
| LLYGLEW | SEQ ID NO. 116 |
| VRPGLRS | SEQ ID NO. 117 |
| IRSGFGS | SEQ ID NO. 118 |
| LRSGRGS | SEQ ID NO. 119 |
| AGFGMLL | SEQ ID NO. 120 |
| VLGFSPW | SEQ ID NO. 121 |
| HRRDHPE | SEQ ID NO. 122 |
| ARGLQRR | SEQ ID NO. 123 |
| GVGARRS | SEQ ID NO. 124 |
| GMIVVGG | SEQ ID NO. 125 |
| RRYSADS | SEQ ID NO. 126 |

Figure 1 (cont.)

| | |
|---|---|
| SELGGGD | SEQ ID NO. 127 |
| AGLSADI | SEQ ID NO. 128 |
| TSGGGIV | SEQ ID NO. 129 |
| VLFQVQP | SEQ ID NO. 130 |
| DRVTGAW | SEQ ID NO. 131 |
| VVEVAST | SEQ ID NO. 132 |
| AVQDPRR | SEQ ID NO. 133 |
| GPVTIDG | SEQ ID NO. 134 |
| FKGPRLM | SEQ ID NO. 135 |
| YRMIADW | SEQ ID NO. 136 |
| FILGVRD | SEQ ID NO. 137 |
| QTTYGDP | SEQ ID NO. 138 |
| GGAVNVY | SEQ ID NO. 139 |
| DVISDPL | SEQ ID NO. 140 |
| VIVGVWF | SEQ ID NO. 141 |
| GGIWVVI | SEQ ID NO. 142 |
| VEAPDGT | SEQ ID NO. 143 |
| LRFVGPR | SEQ ID NO. 144 |
| FDERGSF | SEQ ID NO. 145 |
| AGGTLGV | SEQ ID NO. 146 |
| GTRLVLS | SEQ ID NO. 147 |
| WGVLVRD | SEQ ID NO. 148 |
| KRIEDEP | SEQ ID NO. 149 |
| RRTSIMA | SEQ ID NO. 150 |
| EEFQSPD | SEQ ID NO. 151 |
| LPRAVVE | SEQ ID NO. 152 |
| PYEGPMPW | SEQ ID NO. 153 |
| QGGETGYE | SEQ ID NO. 154 |
| NQSLPSGN | SEQ ID NO. 155 |
| GAQSTSSQ | SEQ ID NO. 156 |
| PSSNRWFP | SEQ ID NO. 157 |
| ALKAYHLP | SEQ ID NO. 158 |
| GESAARVH | SEQ ID NO. 159 |
| QPDNKHLF | SEQ ID NO. 160 |
| TALKPSFH | SEQ ID NO. 161 |
| YNRDTSLM | SEQ ID NO. 162 |
| TSAPTYES | SEQ ID NO. 163 |
| LHHRYQKQ | SEQ ID NO. 164 |
| PYSRNTLC | SEQ ID NO. 165 |
| NCAKLPCV | SEQ ID NO. 166 |
| YALTVNLG | SEQ ID NO. 167 |
| GLSPSGEQ | SEQ ID NO. 168 |
| KNSEAMFT | SEQ ID NO. 169 |
| KWADCRRP | SEQ ID NO. 170 |

Figure 1 (cont.)

| | |
|---|---|
| WPPCGWGCRGR | SEQ ID NO. 171 |
| SISCLWGCGSW | SEQ ID NO. 172 |
| GMGCLGLCGGS | SEQ ID NO. 173 |
| GDGCPEVCVFP | SEQ ID NO. 174 |
| YEMCDLSCVYW | SEQ ID NO. 175 |
| RMPCSVSCDLM | SEQ ID NO. 176 |
| GNSCSLHCYIW | SEQ ID NO. 177 |
| ARLCGGACRGL | SEQ ID NO. 178 |
| GEECAPGCTRG | SEQ ID NO. 179 |
| DVDCRHLCNVH | SEQ ID NO. 180 |
| PQLCGGTCRGL | SEQ ID NO. 181 |
| VAGCPVGCIRG | SEQ ID NO. 182 |
| LGYCSWGCARE | SEQ ID NO. 183 |
| WPACSPECRWP | SEQ ID NO. 184 |
| TAGCGSMCLHV | SEQ ID NO. 185 |
| LFLCVFGCALV | SEQ ID NO. 186 |
| DVQCYVRCSPD | SEQ ID NO. 187 |
| GGVCLGRCLGG | SEQ ID NO. 188 |
| WRVCGALCGPA | SEQ ID NO. 189 |
| SGRCLGVCGWA | SEQ ID NO. 190 |
| AERCRMNCMKP | SEQ ID NO. 191 |
| RKSCSGACVWG | SEQ ID NO. 192 |
| GAACGSGCLHV | SEQ ID NO. 193 |
| TGACIPGCGGW | SEQ ID NO. 194 |
| QAPCVSGCGVD | SEQ ID NO. 195 |
| RRWCGTLCLCW | SEQ ID NO. 196 |
| YITCGHDCVTF | SEQ ID NO. 197 |
| RRSCGFSCVAG | SEQ ID NO. 198 |
| LRVCNVDCMTG | SEQ ID NO. 199 |
| SLFCQIDCVMW | SEQ ID NO. 200 |
| WDVCLSDCVFN | SEQ ID NO. 201 |

Figure 2

| | |
|---|---|
| CCCTCATAGTTAGCGTAACG | SEQ ID NO. 202 |

```
                        SEQUENCE LISTING

<160> NUMBER OF SEQ ID NOS: 208

<210> SEQ ID NO 1
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 1

Ala Arg Pro Gly Leu Arg Ser
1               5

<210> SEQ ID NO 2
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 2

Met Arg Tyr Ala Leu Arg Ser
1               5

<210> SEQ ID NO 3
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 3

Leu Arg Pro Gly Leu Arg Ser
1               5

<210> SEQ ID NO 4
<211> LENGTH: 7
<212> TYPE: PRT
<213> ORGANISM: Homo sapiens
<220> FEATURE:
<221> NAME/KEY: PEPTIDE
<222> LOCATION: (1)..(7)
```

```
<400> SEQUENCE: 4

Leu Arg Ser Gly Ser Gly Ser
1               5

<210> SEQ ID NO 5
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 5

Val Arg Ser Gly Arg Gly Ser
1               5

<210> SEQ ID NO 6
<211> LENGTH: 7
<212> TYPE: PRT
<213> ORGANISM: Homo sapiens
<220> FEATURE:
<221> NAME/KEY: PEPTIDE
<222> LOCATION: (1)..(7)
<220> FEATURE:
<221> NAME/KEY: MISC_FEATURE
<222> LOCATION: (6)..(6)
<223> OTHER INFORMATION: May be fused with GST

<400> SEQUENCE: 6

Gly Ile Tyr Arg Leu Arg Ser
1               5

<210> SEQ ID NO 7
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 7

Gly Val Tyr Ser Leu Arg Ser
1               5

<210> SEQ ID NO 8
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 8

Lys Tyr Pro Phe Asp Lys Leu
1               5

<210> SEQ ID NO 9
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 9

Lys Val Tyr Glu Ser Trp Ser
1               5
```

```
<210> SEQ ID NO 10
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 10

Gly Leu Asp Thr Leu Leu Val
1               5

<210> SEQ ID NO 11
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 11

Gln Ser Arg Met Leu Arg Ile
1               5

<210> SEQ ID NO 12
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 12

Ala Ala Phe Leu Gln Gly Gly
1               5

<210> SEQ ID NO 13
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 13

Arg Ser Tyr Phe Glu Met Leu
1               5

<210> SEQ ID NO 14
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 14

Tyr Leu His Leu Leu Pro Pro
1               5

<210> SEQ ID NO 15
<211> LENGTH: 7
<212> TYPE: PRT
<213> ORGANISM: Homo sapiens
<220> FEATURE:
<221> NAME/KEY: PEPTIDE
<222> LOCATION: (1)..(7)
```

```
<400> SEQUENCE: 15

Arg Pro Thr Leu Ile Thr Pro
1               5

<210> SEQ ID NO 16
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 16

Ala Ser Arg Val Arg Leu Pro
1               5

<210> SEQ ID NO 17
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 17

Met Tyr Val Val His Ala Asp
1               5

<210> SEQ ID NO 18
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 18

Gly Pro Thr Leu Ile Lys Leu
1               5

<210> SEQ ID NO 19
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 19

Ala Pro Ala Leu Tyr His Val
1               5

<210> SEQ ID NO 20
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 20

Ser Val Asp Ser Gln Met Gly
1               5

<210> SEQ ID NO 21
<211> LENGTH: 7
<212> TYPE: PRT
```

<213> ORGANISM: Homo sapiens
<220> FEATURE:
<221> NAME/KEY: PEPTIDE
<222> LOCATION: (1)..(7)

<400> SEQUENCE: 21

Val Val Ser Met Val Gly Val
1               5

<210> SEQ ID NO 22
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 22

His Leu Leu Ala Val Ser Tyr
1               5

<210> SEQ ID NO 23
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 23

Pro Gly Cys Ala Leu Gly Ser
1               5

<210> SEQ ID NO 24
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 24

Ala Ala Gly Glu Trp Ser Gly
1               5

<210> SEQ ID NO 25
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 25

Pro Arg Leu Gly His Gly Ser
1               5

<210> SEQ ID NO 26
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 26

Arg Ala Gly Gly Gly Arg Leu
1               5

<210> SEQ ID NO 27
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 27

Leu Thr Val Arg Ala Val Asp
1               5

<210> SEQ ID NO 28
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 28

Pro Leu Gly Trp Leu Ser Tyr
1               5

<210> SEQ ID NO 29
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 29

Cys His Arg Thr Met Arg Asn
1               5

<210> SEQ ID NO 30
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 30

Leu Arg Gly Gly Ile Gly Val
1               5

<210> SEQ ID NO 31
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 31

Phe Phe Asp Gly Ala Gly Ser
1               5

<210> SEQ ID NO 32
<211> LENGTH: 7
<212> TYPE: PRT
<213> ORGANISM: Homo sapiens
<220> FEATURE:
<221> NAME/KEY: PEPTIDE
<222> LOCATION: (1)..(7)

```
<400> SEQUENCE: 32

Arg Arg Ile Asp Asp Phe Arg
1               5

<210> SEQ ID NO 33
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 33

His Leu Ser Leu Ala Gly Leu
1               5

<210> SEQ ID NO 34
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 34

Arg Pro Arg Thr Asp Thr Tyr
1               5

<210> SEQ ID NO 35
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 35

Phe Ser Gln Gly Lys Leu Ala
1               5

<210> SEQ ID NO 36
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 36

Thr Met Glu Thr Gly Gly Ser
1               5

<210> SEQ ID NO 37
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 37

Gly Val Arg Ser Val Arg Asn
1               5

<210> SEQ ID NO 38
<211> LENGTH: 7
```

```
<212> TYPE: PRT
<213> ORGANISM: Homo sapiens
<220> FEATURE:
<221> NAME/KEY: PEPTIDE
<222> LOCATION: (1)..(7)

<400> SEQUENCE: 38

His Ser Gln Arg Phe Gly Lys
1               5

<210> SEQ ID NO 39
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 39

Val Ser Ala Leu Glu Leu Ser
1               5

<210> SEQ ID NO 40
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 40

Ala Gly Met Val Leu Trp Thr
1               5

<210> SEQ ID NO 41
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 41

Pro Asp Gly Arg Phe Gly Gly
1               5

<210> SEQ ID NO 42
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 42

Glu Ser Pro Ser Arg His Thr
1               5

<210> SEQ ID NO 43
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 43

Ala Arg Gly Phe Pro Gly Val
```

```
1               5

<210> SEQ ID NO 44
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 44

Gln Ser Ser Ser Val Ile Leu
1               5

<210> SEQ ID NO 45
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 45

Arg Trp Thr Ser Ser Arg Ser
1               5

<210> SEQ ID NO 46
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 46

Ala Tyr Thr Asn Phe Val Tyr
1               5

<210> SEQ ID NO 47
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 47

Ser Val Leu Glu Asn Ala Ile
1               5

<210> SEQ ID NO 48
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 48

Leu Val Gly Asn Phe Gly Leu
1               5

<210> SEQ ID NO 49
<211> LENGTH: 7
<212> TYPE: PRT
<213> ORGANISM: Homo sapiens
<220> FEATURE:
<221> NAME/KEY: PEPTIDE
```

```
<222> LOCATION: (1)..(7)

<400> SEQUENCE: 49

Gly Leu Val Gly Ser Arg Val
1               5

<210> SEQ ID NO 50
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 50

Arg Thr Phe Ser Lys Leu Gly
1               5

<210> SEQ ID NO 51
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 51

Gly Ser Ile Val Met Leu Ser
1               5

<210> SEQ ID NO 52
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 52

Ala Gly Gly Gly Leu Leu Arg
1               5

<210> SEQ ID NO 53
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 53

Gly Val Arg Leu Leu Thr Ala
1               5

<210> SEQ ID NO 54
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 54

Trp Gly Ala Glu Trp Ser Ser
1               5

<210> SEQ ID NO 55
```

```
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 55

Val Arg Glu Asp Lys Gly Ile
1               5

<210> SEQ ID NO 56
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 56

Leu Phe Ile Leu Val Ser Gly
1               5

<210> SEQ ID NO 57
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 57

Ala Ser Trp Thr Ala Arg Val
1               5

<210> SEQ ID NO 58
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 58

Gly Arg Phe Met Gly Ala Phe
1               5

<210> SEQ ID NO 59
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 59

Asn Arg Thr Arg Phe Ser Ser
1               5

<210> SEQ ID NO 60
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 60
```

Val Leu Gly Ile Ala Val Ser
1               5

<210> SEQ ID NO 61
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 61

Glu Leu Ala Gln Ala Ile Ser
1               5

<210> SEQ ID NO 62
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 62

Lys Ser Val Gly Gly Leu Gln
1               5

<210> SEQ ID NO 63
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 63

Thr Cys Ser Arg Leu Leu Thr
1               5

<210> SEQ ID NO 64
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 64

Phe Cys Leu Leu Cys His Met
1               5

<210> SEQ ID NO 65
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 65

Asn Arg Gly Arg Gly Tyr Leu
1               5

<210> SEQ ID NO 66
<211> LENGTH: 7
<212> TYPE: PRT
<213> ORGANISM: Homo sapiens
<220> FEATURE:

```
<221> NAME/KEY: PEPTIDE
<222> LOCATION: (1)..(7)

<400> SEQUENCE: 66

Phe Phe Trp Ser Thr Ala Gln
1               5

<210> SEQ ID NO 67
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 67

Phe Leu Phe Trp Gly Arg Thr
1               5

<210> SEQ ID NO 68
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 68

Val Met Leu Ser Thr Gly Pro
1               5

<210> SEQ ID NO 69
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 69

Gly Ile Val Cys Leu Gly Arg
1               5

<210> SEQ ID NO 70
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 70

Gly Val His Ser Arg Cys Gly
1               5

<210> SEQ ID NO 71
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 71

Tyr Arg Gly Phe Pro Pro Pro
1               5
```

```
<210> SEQ ID NO 72
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 72

Ala Arg Gly Met Pro Leu Phe
1               5

<210> SEQ ID NO 73
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 73

Cys Arg Asp Ser Cys Gly Arg
1               5

<210> SEQ ID NO 74
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 74

Gly Leu Leu Cys Gly Arg Asp
1               5

<210> SEQ ID NO 75
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 75

Ile Arg Val Ser Tyr Gly Arg
1               5

<210> SEQ ID NO 76
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 76

Trp Arg Arg Val Gly Asp Leu
1               5

<210> SEQ ID NO 77
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 77
```

```
Leu Gly Ser Gly Ser Trp Pro
1               5

<210> SEQ ID NO 78
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 78

Val Phe Ser Pro Val Asn Pro
1               5

<210> SEQ ID NO 79
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 79

Ser Leu Gln Ser Val Val Ala
1               5

<210> SEQ ID NO 80
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 80

Ile Arg Gly Ile Gly Gly Ala
1               5

<210> SEQ ID NO 81
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 81

Lys Val Phe Ala Arg Leu Gly
1               5

<210> SEQ ID NO 82
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 82

Val Gly Arg Thr Val Ile Gln
1               5

<210> SEQ ID NO 83
<211> LENGTH: 7
<212> TYPE: PRT
<213> ORGANISM: Homo sapiens
```

<220> FEATURE:
<221> NAME/KEY: PEPTIDE
<222> LOCATION: (1)..(7)

<400> SEQUENCE: 83

Gly Leu Pro Arg Leu Ser Gly
1               5

<210> SEQ ID NO 84
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 84

Asp Cys Val Trp Asp Cys Met
1               5

<210> SEQ ID NO 85
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 85

Gly Leu Gly Ile Tyr Val Leu
1               5

<210> SEQ ID NO 86
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 86

Phe Phe Ile Thr Pro Arg Ser
1               5

<210> SEQ ID NO 87
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 87

Met Gly Gly Ser Leu Phe Gly
1               5

<210> SEQ ID NO 88
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 88

Ala Ala Arg Tyr Gly Ile Asp
1               5

```
<210> SEQ ID NO 89
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 89

Trp Arg Arg Ser Glu Arg Thr
1               5

<210> SEQ ID NO 90
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 90

Lys Leu Ser Gly Val Ser Leu
1               5

<210> SEQ ID NO 91
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 91

Trp Val Gly Gly Ile Arg Gly
1               5

<210> SEQ ID NO 92
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 92

Ile Pro Arg Ser Thr Phe Gly
1               5

<210> SEQ ID NO 93
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 93

Val Cys Trp Ala Ser Trp Cys
1               5

<210> SEQ ID NO 94
<211> LENGTH: 7
<212> TYPE: PRT
<213> ORGANISM: Homo sapiens
<220> FEATURE:
<221> NAME/KEY: PEPTIDE
<222> LOCATION: (1)..(7)
```

<400> SEQUENCE: 94

Val Arg Ala Ser Pro Ser Leu
1               5

<210> SEQ ID NO 95
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 95

Pro Leu Leu Tyr Arg Asn Ala
1               5

<210> SEQ ID NO 96
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 96

Leu Arg Ser Gly Arg Gly Ser
1               5

<210> SEQ ID NO 97
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 97

Trp Ala Leu Thr Thr Ala Leu
1               5

<210> SEQ ID NO 98
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 98

Ile Val Phe Gly Arg Gly Ser
1               5

<210> SEQ ID NO 99
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 99

Met Arg Val Phe Gly Gly Val
1               5

<210> SEQ ID NO 100
<211> LENGTH: 7
<212> TYPE: PRT

```
<213> ORGANISM: Homo sapiens
<220> FEATURE:
<221> NAME/KEY: PEPTIDE
<222> LOCATION: (1)..(7)

<400> SEQUENCE: 100

Val Leu Gly Ser Leu Gly Ser
1               5

<210> SEQ ID NO 101
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 101

Leu Trp Ser Glu Pro Met Val
1               5

<210> SEQ ID NO 102
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 102

Glu Arg Ala Pro Leu Lys Ala
1               5

<210> SEQ ID NO 103
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 103

Ile Ser Arg Phe Gly Tyr Val
1               5

<210> SEQ ID NO 104
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 104

Gly Leu Lys Phe Asn Trp Ser
1               5

<210> SEQ ID NO 105
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 105

Lys Ser Ser Glu Ile Pro Arg
1               5
```

<210> SEQ ID NO 106
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 106

Arg Arg Ala Leu Phe Ala Thr
1               5

<210> SEQ ID NO 107
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 107

Gly Trp Arg Gly Leu Arg Thr
1               5

<210> SEQ ID NO 108
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 108

Asp Tyr Phe Trp Phe Ala Asp
1               5

<210> SEQ ID NO 109
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 109

Ser Arg Tyr Trp Thr Arg Ser
1               5

<210> SEQ ID NO 110
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 110

Arg Arg Glu Gly Leu Arg Ser
1               5

<210> SEQ ID NO 111
<211> LENGTH: 7
<212> TYPE: PRT
<213> ORGANISM: Homo sapiens
<220> FEATURE:
<221> NAME/KEY: PEPTIDE
<222> LOCATION: (1)..(7)

```
<400> SEQUENCE: 111

Ser Trp Tyr Thr Leu Arg Ser
1               5

<210> SEQ ID NO 112
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 112

Val Ser Met Ser Arg Ser Leu
1               5

<210> SEQ ID NO 113
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 113

Leu Ala Tyr Arg Leu Arg Ser
1               5

<210> SEQ ID NO 114
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 114

Val Tyr Tyr Gly Leu Arg Arg
1               5

<210> SEQ ID NO 115
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 115

Leu Thr Tyr Arg Leu Arg Ser
1               5

<210> SEQ ID NO 116
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 116

Leu Leu Tyr Gly Leu Glu Trp
1               5

<210> SEQ ID NO 117
<211> LENGTH: 7
```

```
<212> TYPE: PRT
<213> ORGANISM: Homo sapiens
<220> FEATURE:
<221> NAME/KEY: PEPTIDE
<222> LOCATION: (1)..(7)

<400> SEQUENCE: 117

Val Arg Pro Gly Leu Arg Ser
1               5

<210> SEQ ID NO 118
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 118

Ile Arg Ser Gly Phe Gly Ser
1               5

<210> SEQ ID NO 119
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 119

Leu Arg Ser Gly Arg Gly Ser
1               5

<210> SEQ ID NO 120
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 120

Ala Gly Phe Gly Met Leu Leu
1               5

<210> SEQ ID NO 121
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 121

Val Leu Gly Phe Ser Pro Trp
1               5

<210> SEQ ID NO 122
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 122

His Arg Arg Asp His Pro Glu
```

```
1               5

<210> SEQ ID NO 123
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 123

Ala Arg Gly Leu Gln Arg Arg
1               5

<210> SEQ ID NO 124
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 124

Gly Val Gly Ala Arg Arg Ser
1               5

<210> SEQ ID NO 125
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 125

Gly Met Ile Val Val Gly Gly
1               5

<210> SEQ ID NO 126
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 126

Arg Arg Tyr Ser Ala Asp Ser
1               5

<210> SEQ ID NO 127
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 127

Ser Glu Leu Gly Gly Gly Asp
1               5

<210> SEQ ID NO 128
<211> LENGTH: 7
<212> TYPE: PRT
<213> ORGANISM: Homo sapiens
<220> FEATURE:
<221> NAME/KEY: PEPTIDE
```

```
<222> LOCATION: (1)..(7)

<400> SEQUENCE: 128

Ala Gly Leu Ser Ala Asp Ile
1               5

<210> SEQ ID NO 129
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 129

Thr Ser Gly Gly Gly Ile Val
1               5

<210> SEQ ID NO 130
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 130

Val Leu Phe Gln Val Gln Pro
1               5

<210> SEQ ID NO 131
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 131

Asp Arg Val Thr Gly Ala Trp
1               5

<210> SEQ ID NO 132
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 132

Val Val Glu Val Ala Ser Thr
1               5

<210> SEQ ID NO 133
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 133

Ala Val Gln Asp Pro Arg Arg
1               5

<210> SEQ ID NO 134
```

```
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 134

Gly Pro Val Thr Ile Asp Gly
1               5

<210> SEQ ID NO 135
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 135

Phe Lys Gly Pro Arg Leu Met
1               5

<210> SEQ ID NO 136
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 136

Tyr Arg Met Ile Ala Asp Trp
1               5

<210> SEQ ID NO 137
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 137

Phe Ile Leu Gly Val Arg Asp
1               5

<210> SEQ ID NO 138
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 138

Gln Thr Thr Tyr Gly Asp Pro
1               5

<210> SEQ ID NO 139
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 139
```

Gly Gly Ala Val Asn Val Tyr
1               5

<210> SEQ ID NO 140
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 140

Asp Val Ile Ser Asp Pro Leu
1               5

<210> SEQ ID NO 141
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 141

Val Ile Val Gly Val Trp Phe
1               5

<210> SEQ ID NO 142
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 142

Gly Gly Ile Trp Val Val Ile
1               5

<210> SEQ ID NO 143
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 143

Val Glu Ala Pro Asp Gly Thr
1               5

<210> SEQ ID NO 144
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 144

Leu Arg Phe Val Gly Pro Arg
1               5

<210> SEQ ID NO 145
<211> LENGTH: 7
<212> TYPE: PRT
<213> ORGANISM: Homo sapiens
<220> FEATURE:

```
<221> NAME/KEY: PEPTIDE
<222> LOCATION: (1)..(7)

<400> SEQUENCE: 145

Phe Asp Glu Arg Gly Ser Phe
1               5

<210> SEQ ID NO 146
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 146

Ala Gly Gly Thr Leu Gly Val
1               5

<210> SEQ ID NO 147
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 147

Gly Thr Arg Leu Val Leu Ser
1               5

<210> SEQ ID NO 148
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 148

Trp Gly Val Leu Val Arg Asp
1               5

<210> SEQ ID NO 149
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 149

Lys Arg Ile Glu Asp Glu Pro
1               5

<210> SEQ ID NO 150
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 150

Arg Arg Thr Ser Ile Met Ala
1               5
```

```
<210> SEQ ID NO 151
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 151

Glu Glu Phe Gln Ser Pro Asp
1               5

<210> SEQ ID NO 152
<211> LENGTH: 7
<212> TYPE: PRT
<213> ORGANISM: Homo sapiens
<220> FEATURE:
<221> NAME/KEY: PEPTIDE
<222> LOCATION: (1)..(7)

<400> SEQUENCE: 152

Leu Pro Arg Ala Val Val Glu
1               5

<210> SEQ ID NO 153
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 153

Pro Tyr Glu Gly Pro Met Pro Trp
1               5

<210> SEQ ID NO 154
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 154

Gln Gly Gly Glu Thr Gly Tyr Glu
1               5

<210> SEQ ID NO 155
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 155

Asn Gln Ser Leu Pro Ser Gly Asn
1               5

<210> SEQ ID NO 156
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 156
```

```
Gly Ala Gln Ser Thr Ser Ser Gln
1               5

<210> SEQ ID NO 157
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 157

Pro Ser Ser Asn Arg Trp Phe Pro
1               5

<210> SEQ ID NO 158
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 158

Ala Leu Lys Ala Tyr His Leu Pro
1               5

<210> SEQ ID NO 159
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 159

Gly Glu Ser Ala Ala Arg Val His
1               5

<210> SEQ ID NO 160
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 160

Gln Pro Asp Asn Lys His Leu Phe
1               5

<210> SEQ ID NO 161
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 161

Thr Ala Leu Lys Pro Ser Phe His
1               5

<210> SEQ ID NO 162
<211> LENGTH: 8
<212> TYPE: PRT
<213> ORGANISM: Homo sapiens
```

```
<220> FEATURE:
<221> NAME/KEY: PEPTIDE
<222> LOCATION: (1)..(8)

<400> SEQUENCE: 162

Tyr Asn Arg Asp Thr Ser Leu Met
1               5

<210> SEQ ID NO 163
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 163

Thr Ser Ala Pro Thr Tyr Glu Ser
1               5

<210> SEQ ID NO 164
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 164

Leu His His Arg Tyr Gln Lys Gln
1               5

<210> SEQ ID NO 165
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 165

Pro Tyr Ser Arg Asn Thr Leu Cys
1               5

<210> SEQ ID NO 166
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 166

Asn Cys Ala Lys Leu Pro Cys Val
1               5

<210> SEQ ID NO 167
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 167

Tyr Ala Leu Thr Val Asn Leu Gly
1               5
```

```
<210> SEQ ID NO 168
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 168

Gly Leu Ser Pro Ser Gly Glu Gln
1               5

<210> SEQ ID NO 169
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 169

Lys Asn Ser Glu Ala Met Phe Thr
1               5

<210> SEQ ID NO 170
<211> LENGTH: 8
<212> TYPE: PRT
<213> ORGANISM: Homo sapiens
<220> FEATURE:
<221> NAME/KEY: PEPTIDE
<222> LOCATION: (1)..(8)

<400> SEQUENCE: 170

Lys Trp Ala Asp Cys Arg Arg Pro
1               5

<210> SEQ ID NO 171
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 171

Trp Pro Pro Cys Gly Trp Gly Cys Arg Gly Arg
1               5                   10

<210> SEQ ID NO 172
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 172

Ser Ile Ser Cys Leu Trp Gly Cys Gly Ser Trp
1               5                   10

<210> SEQ ID NO 173
<211> LENGTH: 11
<212> TYPE: PRT
<213> ORGANISM: Homo sapiens
<220> FEATURE:
<221> NAME/KEY: PEPTIDE
<222> LOCATION: (1)..(11)
```

<400> SEQUENCE: 173

Gly Met Gly Cys Leu Gly Leu Cys Gly Gly Ser
1               5                   10

<210> SEQ ID NO 174
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 174

Gly Asp Gly Cys Pro Glu Val Cys Val Phe Pro
1               5                   10

<210> SEQ ID NO 175
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 175

Tyr Glu Met Cys Asp Leu Ser Cys Val Tyr Trp
1               5                   10

<210> SEQ ID NO 176
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 176

Arg Met Pro Cys Ser Val Ser Cys Asp Leu Met
1               5                   10

<210> SEQ ID NO 177
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 177

Gly Asn Ser Cys Ser Leu His Cys Tyr Ile Trp
1               5                   10

<210> SEQ ID NO 178
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 178

Ala Arg Leu Cys Gly Gly Ala Cys Arg Gly Leu
1               5                   10

<210> SEQ ID NO 179
<211> LENGTH: 11
<212> TYPE: PRT

```
<213> ORGANISM: Homo sapiens
<220> FEATURE:
<221> NAME/KEY: PEPTIDE
<222> LOCATION: (1)..(11)

<400> SEQUENCE: 179

Gly Glu Glu Cys Ala Pro Gly Cys Thr Arg Gly
1               5                   10

<210> SEQ ID NO 180
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 180

Asp Val Asp Cys Arg His Leu Cys Asn Val His
1               5                   10

<210> SEQ ID NO 181
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 181

Pro Gln Leu Cys Gly Gly Thr Cys Arg Gly Leu
1               5                   10

<210> SEQ ID NO 182
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 182

Val Ala Gly Cys Pro Val Gly Cys Ile Arg Gly
1               5                   10

<210> SEQ ID NO 183
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 183

Leu Gly Tyr Cys Ser Trp Gly Cys Ala Arg Glu
1               5                   10

<210> SEQ ID NO 184
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 184

Trp Pro Ala Cys Ser Pro Glu Cys Arg Trp Pro
1               5                   10
```

<210> SEQ ID NO 185
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 185

Thr Ala Gly Cys Gly Ser Met Cys Leu His Val
1               5                   10

<210> SEQ ID NO 186
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 186

Leu Phe Leu Cys Val Phe Gly Cys Ala Leu Val
1               5                   10

<210> SEQ ID NO 187
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 187

Asp Val Gln Cys Tyr Val Arg Cys Ser Pro Asp
1               5                   10

<210> SEQ ID NO 188
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 188

Gly Gly Val Cys Leu Gly Arg Cys Leu Gly Gly
1               5                   10

<210> SEQ ID NO 189
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 189

Trp Arg Val Cys Gly Ala Leu Cys Gly Pro Ala
1               5                   10

<210> SEQ ID NO 190
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 190

Ser Gly Arg Cys Leu Gly Val Cys Gly Trp Ala
1               5                   10

<210> SEQ ID NO 191
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 191

Ala Glu Arg Cys Arg Met Asn Cys Met Lys Pro
1               5                   10

<210> SEQ ID NO 192
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 192

Arg Lys Ser Cys Ser Gly Ala Cys Val Trp Gly
1               5                   10

<210> SEQ ID NO 193
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 193

Gly Ala Ala Cys Gly Ser Gly Cys Leu His Val
1               5                   10

<210> SEQ ID NO 194
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 194

Thr Gly Ala Cys Ile Pro Gly Cys Gly Gly Trp
1               5                   10

<210> SEQ ID NO 195
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 195

Gln Ala Pro Cys Val Ser Gly Cys Gly Val Asp
1               5                   10

<210> SEQ ID NO 196
<211> LENGTH: 11

```
<212> TYPE: PRT
<213> ORGANISM: Homo sapiens
<220> FEATURE:
<221> NAME/KEY: PEPTIDE
<222> LOCATION: (1)..(11)

<400> SEQUENCE: 196

Arg Arg Trp Cys Gly Thr Leu Cys Leu Cys Trp
1               5                   10

<210> SEQ ID NO 197
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 197

Tyr Ile Thr Cys Gly His Asp Cys Val Thr Phe
1               5                   10

<210> SEQ ID NO 198
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 198

Arg Arg Ser Cys Gly Phe Ser Cys Val Ala Gly
1               5                   10

<210> SEQ ID NO 199
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 199

Leu Arg Val Cys Asn Val Asp Cys Met Thr Gly
1               5                   10

<210> SEQ ID NO 200
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 200

Ser Leu Phe Cys Gln Ile Asp Cys Val Met Trp
1               5                   10

<210> SEQ ID NO 201
<211> LENGTH: 11
<212> TYPE: PRT
<213> ORGANISM: Homo sapiens
<220> FEATURE:
<221> NAME/KEY: PEPTIDE
<222> LOCATION: (1)..(11)

<400> SEQUENCE: 201

Trp Asp Val Cys Leu Ser Asp Cys Val Phe Asn
```

-continued

```
1               5                   10
```

<210> SEQ ID NO 202
<211> LENGTH: 20
<212> TYPE: DNA
<213> ORGANISM: Homo sapiens
<220> FEATURE:
<223> OTHER INFORMATION: Primer

<400> SEQUENCE: 202
ccctcatagt tagcgtaacg                                               20

<210> SEQ ID NO 203
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: RGD-4C

<400> SEQUENCE: 203

Cys Asp Arg Gly Asp Cys Phe Cys
1               5

<210> SEQ ID NO 204
<211> LENGTH: 6
<212> TYPE: PRT
<213> ORGANISM: Homo sapiens
<220> FEATURE:
<221> NAME/KEY: MISC_FEATURE
<222> LOCATION: (1)..(6)
<223> OTHER INFORMATION: From CX6C library

<400> SEQUENCE: 204

Leu Arg Ser Gly Arg Gly
1               5

<210> SEQ ID NO 205
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Family-identifying motif from CX9 collection

<400> SEQUENCE: 205

His Trp Gly Phe
1

<210> SEQ ID NO 206
<211> LENGTH: 14
<212> TYPE: PRT
<213> ORGANISM: Homo sapiens
<220> FEATURE:
<221> NAME/KEY: MISC_FEATURE
<222> LOCATION: (1)..(14)
<223> OTHER INFORMATION: One of a family of peptides which result in
      destruction of mitochondrial membranes

<400> SEQUENCE: 206

Lys Leu Ala Lys Leu Ala Lys Lys Leu Ala Lys Leu Ala Lys
1               5                   10

<210> SEQ ID NO 207
<211> LENGTH: 5
<212> TYPE: PRT

```
<213> ORGANISM: Homo sapiens
<220> FEATURE:
<221> NAME/KEY: MISC_FEATURE
<222> LOCATION: (1)..(5)
<223> OTHER INFORMATION: Conjugate peptide used in chemotherapy

<400> SEQUENCE: 207

Cys Asn Gly Arg Cys
1               5

<210> SEQ ID NO 208
<211> LENGTH: 4
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Shared sequence motif

<400> SEQUENCE: 208

Gly Ser Gly Ser
1
```

METASTASIS-SPECIFIC PEPTIDES AND THEIR DIAGNOSTIC AND THERAPEUTIC APPLICATIONS

STATE-OF-THE ART OF THE INVENTION

The present invention comprises peptides that are highly specific for tumor metastatic cells, in particular cells of hepatic metastases, and their application in the diagnostic and therapeutic fields.

TECHNICAL BACKGROUND OF THE INVENTION

Tumor and Metastatization

Tumorigenesis is a multi-stage process in which some cells progressively evolve toward malignity. The actual knowledge in the field of neoplasia underlines that cancer is a disease induced by dynamic changes of the genome. Through these variations, tumor cells acquire independence from various mechanisms that control the physiological functions of the organism. As a consequence, they become able of (1) growing continuously, (2) inducing the recruitment of endothelial cells for the formation of new blood vessels and (3) colonizing organs different from that of origin.

The proliferative capability of tumor cells is fundamentally due to two mechanisms. First, while normal cells need mitogenic factors to switch from a quiescent condition to an active, proliferating one, in tumor cells mutations and/or overexpression of growth factor receptors can induce the proliferation cascade independently from the presence of a ligand. Moreover, in many cases, tumor cells acquire the ability to synthesize soluble factors they are sensitive to. So, an autocrine stimulation is set up, which further enhances the tumor growth. The other phenomenon of deregulation of the cell growth in tumors is the resistance to apoptosis (programmed cell death). This mechanism, fundamental in the growth and remodeling of organs during the physiological development, is induced also in the case of non-reversible genome damages, to avoid the expansion of aberrant cell population. Some cells, however, can escape this kind of protection and become independent, thus favoring the propagation of mutations and the consequent neoplastic progression.

A primordial tumor mass is constituted by a small cell number, and could not develop over 2 mm in diameter if not sustained by adequate feed and oxygen support. This is the phase in which angiogenesis, the formation of new blood capillaries from pre-existing blood vessels, is strongly stimulated by tumor cells themselves. The unbalance between positive and negative signals of the angiogenesis regulation leads to the neo-formation of a vascular network that penetrates and feeds the actively proliferating tumor mass. Tumor blood vessels, besides providing the nutrition, have the function of carrying malignant cells toward other body districts.

Tumor progression evolves toward an irreversibility stage, whose characteristic feature is metastatization. In this process, pioneer cells escape from the primary tumor mass. Once entered into the capillaries that fill the tumor, they reach the bloodstream, which carries them in regions distant from the site of derivation, where they will give raise to a secondary tumor.

The development of metastasis represents a complex biological event, related to the interactions between intrinsic factors of the organism (general conditions, integrity of the immune response) and specific features of tumor cells (localization, size and histological patterns). From the microscopic primary site, the diffusion of tumor cells is first local, through a centrifugal spreading. By producing proteases that degrade the intercellular connections and the extracellular matrix, tumor cells invade anatomic structures and tissues that are scarcely resistant (fat tissue, nerve sheaths, bone marrow).

A first obstacle to the metastatic diffusion is offered by the presence of relatively impenetrable structures, such as the organ capsules, cartilage or periostium, the meninx. Due to the difficulty of going beyond these boundaries, metastatization in distant sites must follow steps that can be summarized as follows: (1) entrance into the tumor capillary network by a mechanism called "intravasation", (2) transport through the bloodstream, (3) specific recognition of the destination endothelium, (4) exit from the capillary by a mechanism called "extravasation" and (5) metastasis development, supported by active angiogenesis.

The success of dissemination depends on the anatomical features and on the hemodynamic factors of the host organism, and on the interactions that tumor cells undergo with the endothelium lining the blood vessels. The most common pathways of diffusion are the vessels (lymphatic and blood) and the celomatic cavities. Lymphatic vessels are quite easily penetrated, because of the absence of a basal lamina. So, tumor cells can easily transit into the lymph nodes, before entering the venous system through the lymphatic-venous connections. The transport into the vessels can affect both arterious and venous system, even if the venous invasion is more common, because the venous circulation collects the flux exiting from organs. Typical examples are the systemic vein for the lung or the port vein for the liver. The trans-celomatic dissemination instead concerns the pleural cavity of the chest and the peritoneal spaces of the abdomen and pelvis. The most commonly involved site is peritoneum, where, after pouring liquids due to the obstruction of the hepatic veins, tumor cells are collected in the ascitic fluid. Stomach, colon, pancreas and ovary cancers usually take this system.

Tumor metastatic cells express specific molecular determinants that contribute in various ways to the metastasis itself. The distribution of metastasis is not casual, but each tumor has preferential addresses, this is known as organo-tropism. Liver is a target organ for colorectal tumors; bones for prostate and ovary tumors; lungs for testis, bone and breast tumors. Lungs and liver, due to their filter function and to the presence of a huge number of capillaries, can receive metastases virtually from every organ and also send tumor colonies, mainly toward brain and bones.

The liver is a common site for metastatic lesions. The reason has to be searched in the functional and structural organization of the hepatic district. The port vein, which drains the blood to the abdominal viscera, represents the conduct through which the cells coming from the primary tumors are veiculated to the liver. The adhesion of circulating tumor cells to liver endothelium is a critical step for the beginning of metastatization. Hepatic metastases develop as a consequence of the invasion of the hepatic parenchyma by these cell thrombi.

The high volume of hepatic blood flux (about 25% of the cardiac flux), and the particular microscopic anatomy of the sinusoids are the factors that favor the hepatic dissemination. The primary tumor may be localized in the gastro-intestinal tract, i.e. colon, rectum, stomach, pancreas, biliary tract and bowel. To those, also tumors of the breast and lung may be added.

Colorectal Tumor

Different kinds of classification exist that, in general, divide the progressive evolution of the disease in steps characterized by the degree of body invasion of that tumor. The Dukes and MAC (Modified Astler-Coller) classifications, proposed at the beginning of the clinical studies, are now the less used. Generally, the TNM (Tumor Node Metastasis) classification is preferred, which includes four successive stages:

stage I: tumor limited to the mucosa and the sub-mucosa;
stage II: extension to deeper layers of the intestinal wall;
stage III: invasion of sub-sierosa and lymph nodes;
stage IV: metastasis.

The therapeutic approaches more common by now are surgery, chemotherapy and radiotherapy. The kind of clinical strategy is chosen based on the stage in which the pathology is. In general, the following protocols are used:

stage I: surgery (colostomy);
stage II: surgery can be associated to chemotherapy;
stage III: surgery is in any case associated with chemotherapy;
stage IV: palliative treatment with surgery and/or chemotherapy.

Liver is the most frequent site of colonization by primary colorectal cancer. Currently, the only treatment with a curative potential is surgical removal of metastases. However, despite the increasingly effective means of the hepatic surgery, most patients with liver metastases are not amenable for surgery, because of the extension of their tumor mass.

A Different Approach to Cancer Therapy: Attacking Tumor Blood Vessels

The chemotherapic drugs currently used are between the drugs with the most narrow therapeutic window in the whole medical field. As a consequence, the dose of antitumor drugs that can be administered is limited by the toxic effects on normal tissues. This difficulty can be overcome by targeting cytotoxic drugs to the tumor itself. Even if this has been a goal for long time in cancer biology and in oncological medicine, right now only few examples are known in which the target administration of a drug is possible. For example, the use of monoclonal antibodies against tumor antigens had a limited success, since only a few tumor antigens are known and generally antibodies poorly penetrate into tissues. Moreover, since tumor cells are genetically instable and growth-advantageous mutations accumulate, tumor cell-targeted treatments are generally followed by clonal selection of resistant cells.

The targeting of therapy to the tumor vascular network allows to overcome some of the problems related to traditional therapy. Endothelial cells in the tumor vascular system express molecules peculiar of anogiogenic vessels. Vascular targeting offers several advantages. First, endothelial lining is easily accessible. On the contrary, a tumor-targeted drug needs to diffuse on long distances, penetrate into tightly bound tumor cells and in a very dense stroma, and contrast a very high interstitial pressure. Second, since tumor cells depend on blood supply for their growth, a tumor therapy addressed to the vessels does not need to lead to the destruction of all the endothelial cells. Indeed, endothelium-target therapy has an intrinsic amplification mechanism. Finally, since endothelial cells are diploid and not transformed, it is improbable that they loose the expression of a surface receptor or acquire drug resistance through mutations and clonal evolution. Some endothelial markers have been recently identified. Among these molecules there are some integrins, particularly $\alpha v \beta 3$ and $\alpha v \beta 5$ and endothelial tyrosine kinase receptors with their cognate ligands (VEGF receptors and the various VEGFs, Tie1, Tie2 and angiopietins).

Peptides that Target a Mouse Model of Human Tumor: Discovery of Tumor Endothelial Markers By phage display studies performed in vivo in different animal models peptide sequences have been identified which are able to selectively target tumor vascularization. These sequences proved to be a valid instrument to characterize tumor endothelium and its specific molecular determinants, and to develop biotechnological applications in tumor therapy.

In this way, recurrent peptide sequences have been identified, such as RGD (Arginin-Glycin-Aspartic acid) and NGR (Asparagin-Glycin-Arginin). The RGD motif is embedded in the sequence of several proteins of the extracellular matrix and represents their interaction site with integrins. A phage that presents the CDRGDCFC (SEQ ID NO: 203) sequence, named RGD-4C, is able to specifically target breast tumors, and to selectively bind the $\alpha v \beta 3$ and $\alpha v \beta 5$ integrins. In vitro experiments demonstrated that RGD-containing peptides inhibit cell-cell adhesion thus inducing apoptosis. So, it has been thought that the RGD peptide, without further modification, can act as an antiangiogenic drug, leading to cell death after disruption of the cell-matrix interactions. Also the NGR peptide binds integrins, even if with minor affinity compared to RGD. The specific receptor for the NGR sequence has been successively identified in another membrane protein, aminopeptidase N (APN), overexpressed in vascular structures in active angiogenesis and not detectable in quiescent endothelium. It has been demonstrated that APN specific antibodies can inhibit retinal neovascularization induced by hypoxia in the mouse. In the same way, mice treated with anti-APN antibodies have breast tumors strongly regressed compared to the control group.

In another set of studies peptides that specifically bind the NG2 proteoglycan have been identified, a mouse homolog of HMP (human melanoma proteoglycan), also known as Molecular Weight Melanoma-Associated Antigen. This proteoglycan is mainly expressed by glial progenitor cells, skeletal muscle and cartilage. After the differentiation, the NG2 surface expression is lost. In adults, its presence is limited to vessels in active angiogenesis in some tumor kinds, among which glioblastoma, condrosarcoma, melanoma, and some leukemias. In a nude mice bearing a malignant melanoma, an anti-NG2 antibody conjugated with doxorubicin suppresses tumor growth.

Peptides as Antitumor Drugs

Remodeling of the extracellular matrix is common both to endothelial activation and neoplastic invasion, and need the action of particular enzymes called Matrix Metallo-Proteases (MMP). These proteases, overexpressed in the tumor, are almost absent in normal tissues, except in cell migration and tissue remodeling events during morphogenesis. Synthetic inhibitors of two such proteases, MMP-2 (Gelatinase A; 72 Kd) and MMP-9 (Gelatinase B; 92 Kd), which are the more strictly involved proteases in angiogenesis and metastatic potential, have been isolated by phage display. From this study, it has been shown that the most represented clones express the LRSGRG (SEQ ID NO: 204) sequence derived from a CX6C library. Another protein family, identified from a CX9 collection, is the one with the HWGF (SEQ ID NO: 205) motif. Soluble peptides containing the HWGF (SEQ ID NO: 205) motif show in vitro inhibitory activity against MMP-9. These peptides inhibit the migration of tumor cell lines and of endothelial cells derived from human umbilical cord. In vivo, they are efficient in inhibiting tumor growth and in preventing the appearance of metastases.

Use of Peptides in Biotechnologically Innovative Antitumor Therapies

As described previously, peptides specifically associated to tumor endothelial markers or tumor cells have been successfully employed in therapeutic protocols in the mouse. A second approach has been investigated, conjugating RGD-4C and CNGRC (SEQ ID NO: 207) peptides to the chemotherapic drug doxorubicin, and using this compound for the treatment of breast tumors in mice. Animals subjected to this therapy survived up to six months, demonstrating that this compound is able to inhibit both primary tumor and metastasis development with higher efficacy and lower toxicity compared to systemic administration.

In a third set of applications, chimeric peptides have been made, which possess two functional domains. The former can selectively bind to the target cell and be internalized; the latter is pro-apoptotic, non toxic in body fluids but only in the intracellular environment. More than 100 peptides exist that act causing the destruction of mitochondrial membranes and induction of apoptosis. Among these, a 14 aa sequence has been selected, KLAKLAKKLAKLAK (SEQ ID NO: 206), which demonstrated to have a strong antibiotic potential in the form of D-enantiomer. The peptides RGD-4C and CNGRC (SEQ ID NO: 207) have been coupled to this peptide. It has been found that these compounds cause mitochondrial alterations and lead to morphological variations typical of an apoptotic status, such as condensation and fragmentation of the nuclear structures. These results have been confirmed in vivo: mice to which the antitumor agent has been administered show tumors of reduced size and survive for several months.

GENERAL DESCRIPTION OF THE INVENTION

The appearance of metastases is a prognostic factor unfavorable in tumor progression. So, it is fundamental to develop methods that allow to detect and attack early (also sub-clinical dimensioned) metastases. In most cases, the histo-pathological methods currently employed for diagnosis allow to follow the localization of metastases when they are no longer treatable. Further, from a therapeutic point of view, present approaches are limited mainly due to the unspecific toxicity of chemotherapic drugs.

Metastatic cells have peculiar characteristic, compared both to the primary tumors and to the tissues in which they localize. In the same way, tumor blood vessel cells (endothelial cells) are different from normal quiescent ones. In particular, significant modifications involve the cell surfaces, on which molecules are expressed or modified to favor the adaptation to the new environment. Classical methods of study, however, have been proven inefficient to front the problem of the multiplicity of these modifications.

The present invention has the aim of providing a solution to overcome the deficiencies of the state of the art.

According to the present invention, this aim is achieved by peptides as defined in the appended claims, particularly with peptides comprising a sequence as shown in SEQ ID NO: 1-201. The invention also concerns the use of such peptides in the therapeutic and diagnostic field. The appended claims are part of the technical advance given here in relation to the invention.

Preferably, the present invention concerns peptides that specifically recognize hepatic metastatic cells. The invention also concerns the use of conjugates and formulations of such peptides, when they are bound to a diagnostic agent (for example, a label) or to a therapeutic agent (for example, a chemotherapic, a radioactive isotope, a toxin), respectively, for the localization both in vitro and in vivo of hepatic metastatic cells and for the therapy in a tumor bearing subject.

The present invention can provide peptides with high binding selectivity toward metastatic cells, particularly to hepatic metastatic cells thus allowing an efficient localization of such cells both in vitro and in vivo, so that they can be successfully employed both for diagnosis and for therapy of tumors that metastasize in the liver, more particularly, primary colorectal cancers.

Some peptides of the invention share common sequence motifs, such as GGG, RGL, GRL, GSG, LGR, GLS, SAD, YED, LRS and/or GSGS (SEQ ID NO: 208). A preferred common sequence motif is LRS.

Beyond the therapeutic approach, peptides that selectively recognize hepatic metastatic cells represent a useful mean to identify metastases themselves. The small size of these peptides is very advantageous for this kind of application. For example, radionuclide- or fluorescent-conjugated peptides according with the present invention can be used in patients with occult tumors or with non-specific radiological results. Moreover, they can be used for in vivo applications, such as for example magnetic resonance or TAC, after conjugation with suitable molecules for their visualization by any known visualization technique, particularly a technique suitable for an individual body region.

Details on formulation techniques and conjugate administration are known in the art and do not need a detailed description here, being dispensable for the understanding of the invention.

The inventors of the present invention used a proteomic approach (phage display) to characterize the molecular determinants expressed on the surface of cells derived from human hepatic metastases secondary to colorectal carcinomas. Such technique allowed the isolation of peptides that can interact with membrane molecules exclusively present on these cells. The identification of peptides that recognize molecular determinants not present in normal tissues or in the primary tumor allows to use such peptides both for diagnostic and therapeutic applications. From a diagnostic point of view, these peptides, suitably labeled, can be used for the detection of hepatic metastases also in pre-clinical stages. From a therapeutic point of view, it is possible to conjugate them with chemotherapeutic drugs in order to set up protocols of target therapy.

BRIEF DESCRIPTION OF THE DRAWINGS

FIG. 1 illustrates the sequences of the peptides that bind the hepatic metastatic cells according with the present invention, particularly the SEQ ID NO:1-7 represent the peptides that have been deeply studied, selected in the experiments on patients 16, 17 and 18; SEQ ID NO:8-19 represent the peptides selected in the III round of selection on sample from patient 2; SEQ ID NO:20-39 represent the peptides selected in the II round of selection on sample from patient 6; SEQ ID NO:40-64 represent the peptides selected in the III round of selection on sample from patient 7; SEQ ID NO:65-78 represent the peptides selected in the II round of selection on sample from patient 8; SEQ ID NO:79-95 represent the peptides selected in the II round of selection on sample from patient 16; SEQ ID NO:96-107 represent the peptides selected in the III round of selection on sample from patient 16; SEQ ID NO:108-109 represent the peptides selected in the III round of selection on sample from patient 17; SEQ ID NO:110-118 represent the peptides selected in the III round of selection on sample from patient 18; SEQ ID NO:119-122 represent the peptides selected in the IV round of selection on sample from patient 19; SEQ ID NO:123-140 represent the peptides selected in the IV round of selection on sample from patient 9; SEQ ID NO:141-152 represent the peptides selected in the IV round of selection on sample from patient 21; SEQ ID NO:153-170 represent the peptides selected in the II round of selection on sample from patient 23; SEQ ID NO:171-186 represent the peptides selected in the IV round of selection on sample from patient 5; SEQ ID NO:187-201 represent the peptides selected in the II round of selection on sample from patient 8.

FIG. 2 illustrates the nucleotide sequence of the primer used for sequencing the oligonucleotide insert in the phage DNA;

DETAILED DESCRIPTION OF THE INVENTION

Figure 3:
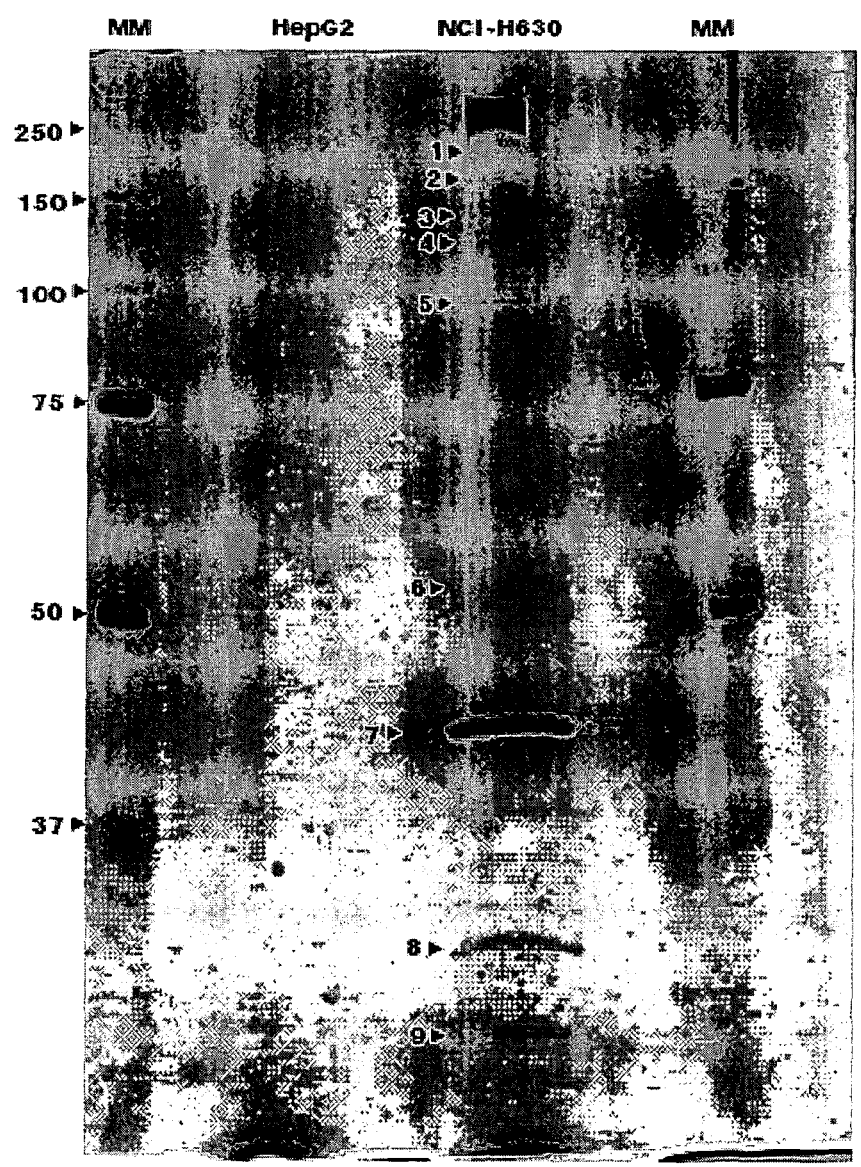
FIG. 3 illustrates a picture of the polyacrylamide gel in which proteins bound to the peptide GIYRLRS (SEQ ID NO: 6) fused to a GST sequence have been separated.

The invention will be now described in details, as a non-limiting example.

Peptides identified in this invention can be used as molecular tools both in diagnostic and in therapeutic fields. It is well known that actual therapeutic approaches in clinical oncology are characterized by low selectivity. A chemotherapeutic agent circulating into the bloodstream affects, other than the tumor masses, all the body cell populations in active proliferation. On the contrary, a peptide that is specifically recognized by surface receptors specific for a particular cell type will be able to address a chemotherapeutic drug preferentially to that kind of cells. Peptides described in the present invention can therefore be successfully employed as drug targeting agent to hepatic metastases.

Moreover, peptides labeled with a detection molecule can be used in the diagnostic field. Presently, detection techniques are used that allow the resolution of a very precocious metastatic lesion from the surrounding tissues. The technology that exploits the use of labeled peptides for the detection of tumor cells is instead based on the molecular differences that distinguish these cells from the others. The peptides according with the present invention can detect even single cells of human hepatic metastases.

Data collected on peptides of the present invention can be summarized as follows:

1) peptides selected in the present application share a high sequence homology between each other, indicating the specificity of the selection;

2) peptides of the present invention have high homology with motifs present in proteins specific for the hepatic tissue and/or related to neoplastic pathologies;

3) from the binding assays it appears that the peptides have high specificity for surface molecules exposed on human hepatic metastatic cells, both primary and in culture, while they preferably do not show affinity for primary cells of normal liver or for cell lines of primary tumors or other kinds of metastases;

4) peptides of the present invention bind universally to cells of hepatic metastases independently from the metastatic stage, clinical parameters to other characteristics related to each patient, thus being good diagnostic-prognostic and therapeutic candidate tools.

A. DEFINITIONS

As used herein in the specification, "a" or "an" may mean one or more. As used herein in the claim(s), in conjunction with the word "comprising," the words "a" or "an" may mean one or more than one. As used herein "another" may mean at least a second or more of an item.

1. Targeting Moiety

A "targeting moiety" is a term that encompasses various types of affinity reagents that may be used to enhance the localization or binding of a substance to a particular location in an animal, including organs, tissues, particular cell types, diseased tissues or tumors. Targeting moieties may include peptides, peptide mimetics, polypeptides, antibodies, antibody-like molecules, nucleic acids, aptamers, and fragments thereof. In certain embodiments, a targeting moiety will enhance the localization of a substance to cells of hepatic metastases secondary to colon carcinoma, through the binding to surface protein of these cells, i.e. through the binding to transmembrane or surface-associated or secreted or extracellular matrix-associated proteins. Selective binding of a targeting moiety of the present invention, e.g., a targeting peptide or antibody, as well as variants and fragments thereof is when the targeting moiety binds a target (e.g. cells of the hepatic metastasis secondary to colon cancer) and does not significantly bind to unrelated cells. A targeting moiety is still considered to selectively bind even if it also binds to other proteins that are not substantially homologous with the target so long as such proteins share homology with a fragment or domain of the peptide target of the antibody. In this case, it would be understood that target moiety binding to the target is still selective despite some degree of cross-reactivity. Typically, the degree of cross-reactivity can be determined and differentiated from binding to the target.

2. Targeting Peptide

A "targeting peptide" is a peptide comprising a contiguous sequence of amino acids, which is characterized by selective localization to an organ, tissue or cell type, which includes specific binding with an extracellar protein or molecule that is specifically expressed or produced in a specific tissue or cell type(s).

3. Receptor

A "receptor" for a targeting peptide includes but is not limited to any molecule or molecular complex that binds to a targeting peptide. Non-limiting examples of receptors include peptides, proteins, glycoproteins, lipoproteins, epitopes, lipids, carbohydrates, multi-molecular structures, and specific conformation of one or more molecules. In preferred embodiments, a "receptor" is a naturally occurring molecule or complex of molecules that is present on the luminal surface of cells forming blood vessels within a target organ, tissue or cell type. More specifically, a "receptor" is a naturally occurring molecule that is present on the luminal surface of cells that form blood vessels into a target organ, tissue or cell type.

4. Amino Acid Residue

An "amino acidic residue" refers to any natural amino acid, any amino acid derivative or any amino acid mimetic that is known in the art. Protein residues are generally consecutive, without non-amino acids that interrupt the sequence of amino acid residues. In particular embodiments, the amino acidic sequence may include one or more non-amino acids. In particular embodiments, the amino acidic sequence may include one or more non-amino acids. In particular embodiments, the sequence of a peptide of the present invention may be interrupted by one or more non-amino acids. Modified or unusual amino acids include but are not limited to: Aad, 2-Aminoadipic acid; EtAsn, N-Ethylasparagine; Baad, 3-Aminoadipic acid, Hyl, Hydroxylysine; Bala, beta-alanine, beta-Aminopropionic acid; AHyl, allo-Hydroxylysine; Abu, 2-Aminobutyric acid; 3Hyp, 3-Hydroxyproline; 4Abu, 4-Aminobutyric acid, piperidinic acid; 4Hyp, 4-Hydroxyproline; Acp, 6-Aminocaproic acid, Ide, Isodesmosine; Ahe, 2-Aminoheptanoic acid; Alle, allo-Isoleucine; Aib, 2-Aminoisobutyric acid; MeGly, N-Methylglycine, sarcosine; Baib, 3-Aminoisobutyric acid; MeIle, N-Methylisoleucine; Apm, 2-Aminopimelic acid; MeLys, 6-N-Methyllysine; Dbu, 2,4-Diaminobutyric acid; MeVal, N-Methylvaline; Des, Desmosine; Nva, Norvaline; Dpm, 2,2'-Diaminopimelic acid; Nle, Norleucine; Dpr, 2,3-Diaminopropionic acid; Orn, Ornithine; and EtGly, N-Ethylglycine. Also included are the D-amino acids.

5. Protein or Peptide

The term "protein or peptide" includes amino acid sequences constituted by at least one of the 20 common amino acids that can be found in natural proteins, or at least a modified or unusual amino acid.

6. Cross-Linking Reagents

Bifunctional "cross-linking reagents" have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

7. Antibodies

As used herein, the term "antibody" is intended to refer broadly to any immunologic binding agent such as IgG, IgM, IgA, IgD and IgE or antibody like molecule. Generally, IgG and/or IgM are preferred because they are the most common antibodies in the physiological situation and because they are most easily made in a laboratory setting. Means for preparing and characterizing antibodies are also well known in the art. It is here defined "antibody" any molecule similar to an antibody that has an antigen binding region, including antibody fragments such as Fab', Fab, F(ab')2, single-domain antibodies (DABs), Fv, single chain antibodies (scFv).

8. Nucleic Acids

"Nucleic acids" according to the present invention may encode a targeting peptide, a targeting antibody, a therapeutic polypeptide a fusion protein or other protein or peptide. The nucleic acid may be derived from genomic DNA, complementary DNA (cDNA) or synthetic DNA. The term "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide. It is contemplated that targeting peptides, targeting antibodies, and fusion proteins may be encoded by any nucleic acid sequence that encodes the appropriate amino acid sequence. The design and production of nucleic acids encoding a desired amino acid sequence is well known to those of skill in the art, using standardized codon tables.

9. Delivery Tools

Several delivery tools can be used for the administration of target peptides according with the present invention; among the others, liposomes and oil-in-water or water-in-oil micro-emulsion systems. The liposomes and the micro-emulsions, and other micro-delivery systems, can be prepared by procedures well known in the art. Ligands may be bound covalently to sites on the liposome surfaces. The number and surface density of these sites may be adjusted by employing specific liposome formulations and/or liposome types. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl) carbodiimide (EDC).

B. PROTEINS AND PEPTIDES

1. Peptides

In one embodiment, the present invention involves the use of a peptide capable of selectively binding to metastatic cells, preferably hepatic metastatic cells. The peptide may comprise a single copy of a sequence as defined in SEQ ID NO. 1-201 or multiple identical or different copies of such sequences optionally connected by amino acid linker sequences.

Due to their relatively small size, target peptides of the present invention can be synthesized in solution or on solid supports, according to well known techniques. Short peptides, generally from about 6 to 35-40 amino acids, can be easily produced with these techniques. Alternatively, recombinant cDNA technology can be used, in which a nucleotidic sequence coding for a peptide of the invention is inserted in an expression vector, transformed or transfected in proper host cells, and cultured in conditions suitable for protein expression.

The peptides of the present invention can consist of natural amino acid residues or may comprise at least one modified or unusual amino acid residue. The peptides of the present invention may be linear or cyclic peptides. The peptides of the present invention preferably have a length of about 6 to about 100, preferably to about 35-40 amino acids or amino acid mimetics.

2. Peptidomimetics

Another embodiment of the present invention involves the use of "peptidomimetics". Mimetics are peptides containing molecules that mimic elements of the secondary structure of the proteins. The ratio at the basis of peptidomimetics is in the fact that protein peptide backbone has mainly the function of orienting the side chains of the amino acids, in order to favor the molecular interactions, such as those of the antibodies and antigens. A peptidomimetic allows the molecular interactions in a same way as in the natural molecule. These principles can be exploited to engineer second generation molecules, having most of the natural properties of the target peptides described in the present invention, but with modified and possibly improved characteristics. An example of peptidomimetics is a retroinverted peptide, formed by D-amino acids in inverted sequence compared to the peptide sequence that it mimics. The peptidomimetics of the present invention preferably have a length of about 6 to about 100, preferably to about 35-40 amino acids or amino acid mimetics.

3. Fusion Proteins

Peptides of the present invention can also be used as one of the components of a fusion protein.

Fusion proteins comprise the whole sequence or a portion of the target peptide fused at its N- and/or C-terminus optionally via a peptidic linker to a second polypeptide or protein, which is heterologous to the target peptide. For example, fusion proteins may comprise signal sequences of other proteins, to allow the expression of recombinant proteins in an heterologous host. Other useful fusion proteins comprise an immunologically active domain, such as an antibody epitope, to facilitate the purification of the fusion protein. The incorporation of a cleavage site, e.g. a proteolytic cleavage site, at the fusion site or in the immediate vicinity will favor the removal of the exogeneous domain after purification. Other useful fusion proteins comprise functional domains, such as active sites of enzymes, glycosylation domains, cell addressing signals, or transmembrane regions.

In one embodiment of the present invention, fusion proteins are made by target peptides fused to a protein or a peptide with therapeutic activity. Examples of proteins or peptides that can be incorporated in a fusion protein include: cytostatic proteins, cytotoxic proteins, pro-apoptotic agents, antiangiogenic agents, hormones, cytokines, growth factors, peptide drugs, antibodies, Fab fragments of antibodies, antigens, receptor proteins, enzymes, lectins, proteins of the major histocompatibility complex, cell adhesion proteins and binding proteins. Such examples are not intended to be limiting, but it is understood that, accordingly with the present invention, virtually any protein or peptide can be incorporated into a fusion protein that includes a target peptide. Methods to produce fusion proteins are well known. Such proteins can be produced, for example, by chemical bound using bifunctional cross-linking reagents, by de novo synthesis of the whole fusion protein, or by attachment of a sequence of DNA coding for the target peptide to a sequence of DNA coding for the second protein or peptide, followed by the expression of the whole fusion protein.

4. Antibodies

In a different embodiment of the present invention, it may be desirable to produce antibodies against target peptides object of the present invention.

For this purpose, the target peptides, or the molecules they bind, can be coupled, bound, conjugated or chemically linked to one or more agents by spacers, poly-spacers, or derivatized amino acids to produce a complex comprising at least one target peptide or molecule which binds to a target peptide. This can be done in such a way that a bi- or multivalent complex is produced, or a vaccine. Methods for producing such complexes are familiar to those skilled in the art, and can be adapted to human administration, i.e. pharmacologically acceptable. Preferred agents are carriers, like hemocyanin (KLH) and bovine serum albumin (BSA). The resulting antibodies can be used both for diagnosis and therapy, for example by binding and/or inhibiting functional proteins on the surface of metastatic cells.

To improve the efficiency of antibody molecules, they may be bound or complexed to at least one system or molecule, for example a molecule that allows its detection. Non-limiting examples of such molecules include enzymes, radionuclides, aptamers, fluorescent labels, phosphorescent molecules, chemiluminescent molecules, chromophores, luminescent molecules, colored particles or ligands such as biotin.

C. DIAGNOSTIC AND THERAPEUTIC CONJUGATES

In an embodiment of the present invention, it may be desirable to couple specific bioactive agents to one or more target peptides accordingly to the present invention for the specific release into an organ, tissue or cell type. Below are indicated some examples of agents that can be coupled to target peptides accordingly to the present invention.

Conjugates according to the present invention can be produced by direct conjugation of the target peptide to the therapeutic or diagnostic agent of interest, or using cross-linking reagents to establish a binding between a peptide and the molecule of interest.

1. Cytokines

The term "cytokine" is a generic term for proteins released by one cell population that act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor and LT. As used herein, the term "cytokine" includes proteins from natural sources or from recombinant cell culture and biologically active equivalents of the native sequence cytokines.

2. Chemokines

"Chemokines" generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines.

3. Imaging Agents

In certain embodiments, the targeting moieties of the present invention may be attached to imaging agents of use for imaging and diagnosis of hepatic metastases.

Several imaging agents are well known, as are the methods to bind them to proteins or peptides. Non-limiting examples of imaging agents include paramagnetic ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of use as imaging or therapeutic agents include $^{211}$astatine, $^{14}$-carbon, $^{51}$chromium, $^{36}$-chlorine, $^{57}$cobalt, $^{58}$cobalt, $^{67}$copper, $^{152}$Eu, $^{67}$gallium, $^{3}$hydrogen, $^{123}$iodine, $^{125}$iodine, $^{131}$iodine, $^{59}$iron, $^{32}$phosphorus, $^{186}$rhenium, $^{188}$rhenium, $^{75}$selenium, $^{35}$sulphur, $^{99m}$techneticum and $^{90}$yttrium.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art.

In still further embodiments, a targeting moiety may be operatively coupled to a nanoparticle. Nanoparticles include, but are not limited to colloidal gold and silver nanoparticles. Metal nanoparticles exhibit colors in the visible spectral region. Further examples of nanoparticles are magnetic nanoparticles.

4. Therapeutic Agents

In certain embodiments, therapeutic agents may be operatively coupled to a targeting peptide or fusion protein for selective delivery to, for example, tumor vasculature of the hepatic metastases. Agents or factors suitable for use may include any chemical compound that induces apoptosis, cell death, cell stasis and/or anti-angiogenesis, such as:

Regulators of Programmed Cell Death or Apoptosis. The Bcl-2 protein and other members of the family are involved in apoptosis, and can be classified as agonists or antagonists of apoptosis. For example, Bcl-2 and other members of the family (e.g., Bcl-XL, Bcl.-W, Bcl-S, Mcl-1, A1, Bfl-1) are pro-apoptotic, while others (e.g., Bax, Bak, Bik, Bim, Bid, Bad, Harakiri) are anti-apoptotic.

Inhibitors of angiogenesis. In certain embodiments the present invention may concern administration of targeting moieties operatively coupled to anti-angiogenic agents, such as angiotensin, laminin peptides, fibronectin peptides, plasminogen activator inhibitors, tissue metalloproteinase inhibitors, interferons, interleukin 12, platelet factor 4, IP-10, thrombospondin, 2-methoxyestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, accutin, angiostatin, cidofovir, vincristine, bleomycin, AGM-1470, platelet factor 4 or minocycline.

Cytotoxic agents. Chemotherapeutic (cytotoxic) agents may be used to treat various disease states, including cancer. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Alkylating agents. Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, a nitrogen mustard, an ethyleneimine, a methylmelamine, an alkyl sulfonate, a nitrosourea or a triazine. They include but are not limited to: busulfan, chlorambucil, cisplatin, cyclophosphamide (cytoxan), dacarbazine, ifosfamide, mechlorethamine (mustargen), and melphalan.

Antimetabolites. Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

Natural products. Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors. Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine. Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules. Vinca alkaloids are a type of plant alkaloid identified to have pharmaceutical activity. They include such compounds as vinblastine (VLB) and vincristine.

Antibiotics. It is well known that certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin), plicamycin (mithramycin) and idarubicin.

Miscellaneous Cytotoxic Agents. Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

D. NUCLEIC ACIDS

Nucleic acids accordingly to the present invention can code for a target peptide, a target antibody, a therapeutic polypeptide, a fusion protein or other proteins or peptides. The nucleic acid can be selected from genomic DNA, complementary DNA (cDNA), synthetic DNA or RNA.

In one embodiment, the present invention involves the use of vectors expressing a peptide according to the present invention for gene therapy. Gene therapy vectors can include several transgenes including a DNA or RNA sequence coding for at least a peptide or polypeptide of the present invention operatively linked to expression control sequences.

Gene therapy can be used to express a therapeutic gene, for example to enhance or decrease neo-vascularization. DNA may be in form of cDNA, in vitro polymerized DNA, plasmid DNA, parts of a plasmid DNA, genetic material derived from a virus, linear DNA, vectors (P1, PAC, BAC, YAC, artificial chromosomes), expression cassettes, chimeric sequences, recombinant DNA, chromosomal DNA, an oligonucleotide, anti-sense DNA, or derivatives of these groups. RNA may be in the form of oligonucleotide RNA, tRNA (transfer RNA), snRNA (small nuclear RNA), rRNA (ribosomal RNA), mRNA (messenger RNA), in vitro polymerized RNA, recombinant RNA, chimeric sequences, anti-sense RNA, siRNA (small interfering RNA), ribozymes, or derivatives of these groups. An anti-sense polynucleotide is a polynucleotide that interferes with the function of DNA and/or RNA. Antisense polynucleotides include, but are not limited to: morpholinos, 2'-O-methyl polynucleotides, DNA, RNA and the like. SiRNA comprises a double stranded structure typically containing 15-50 base pairs and preferably 21-25 base pairs and having a nucleotide sequence identical or nearly identical to an expressed target gene or RNA within the cell. Interference may result in suppression of expression. The polynucleotide can also be a sequence whose presence or expression in a cell alters the expression or function of cellular genes or RNA. In addition, DNA and RNA may be single, double, triple, or quadruple stranded.

Materials and Methods

The Phage Display Methodology

Phage display is a technique developed in the middle 80' by George Smith of the University of Missouri. The principle consists in selecting peptides from a collection, or library, in which virtually all the possible amino acid permutations are represented. Such peptides are selected based on their ability to specifically bind a target of whatever nature and complexity. The phage display methodology involves rounds of screening and amplification of bound particles, with the aim of obtaining a reduction in diversity and an increase in binding specificity.

The construction of a phage library involves the use of M13 filamentous bacteriophages that can infect *Escherichia coli* bacteria. Peculiar characteristic of these phages is to have a circular single stranded DNA genome, which can be manipulated with the molecular biology techniques. In such a library, the peptides derive from the transcription and translation of random exogenous oligonucleotides, which are cloned into the viral DNA upstream from the gene for the capsid protein pIII. Bacteria are transformed with these constructs by electoporation; so, they will produce a population of recombinant phages, each of which will include a different peptide as a fusion with the pIII protein. With this system it is possible to produce a library with a diversity of about $10^8$-$10^9$ peptides, in which each sequence is represented up to 100-1,000 times. If the degeneration of the sequence is complete (Xn, where X=any amino acid, n=number of the amino acids), each of the 20 amino acids has the same theoretic probability of being included into the sequence. Another possibility is to establish fixed positions for an amino acid. Libraries are frequently characterized by cysteins placed in preferential positions, at both ends of the peptide or intercalated into the random residues, among which intermolecular disulfide bridges are formed that render the peptide circular. Circularization of the insert allows a better exposition of the sequence.

ABBREVIATIONS AND SOLUTIONS

AEC 3-Amino-9-Ethyl Carbazole
Amp Ampicillin
BSA Bovine Serum Albumin
DMEM Dulbecco's Minimal Essential Medium
DMEM/FCS/HEPES High Glucose DMEM/2% FCS/20 mM HEPES
DMSO Dimethylsulfoxide
DTT Dithiothreitol
EDTA Ethylene Diamino Tetracetic Acid
FCS Fetal Calf Serum
GST Glutathione Sulfo-Transferase
HEPES N2-Hydroxy Ethyl piperazino-N'-2-Ethyl Sulfonic Acid
HRP Horseradish Peroxidase
Kan Kanamycin
IPTG Isopropyl-β-Thio Galactoside
LB Luria Bertani Broth
PAF Paraformaldehyde
PBS Phosphate Buffer Saline, 150 mM NaCl, 10 mM $KH_2PO_4$, pH 7.40
PEG/NaCl 20% Poly Ethylene Glycole-8,000, 4 M NaCl
PMSF Phenyl Methyl Sulfonyl Fluoride
SDS Sodium Dodecyl Sulfate
TAE 40 mM Tris-HCl, 0.12% Acetic Acid, 1 mM EDTA
BufferA 50 mM Tris-HCl, pH 7.40, 150 mM NaCl, 5% Glycerol, 2 mM DTT
Buffer H 10 M Tris-HCl, Ph 7.40, 10 mM NaCl, 10 mM PMSF
TBS Tris Buffer Saline, 150 mM NaCl, 2.8 mM KCl, 25 mM Tris base, pH 7.40
TBS-T TBS-0.1%, Tween-20
TB Terrific Broth
Tet Tetracylin
TE 10 mM Tris-HCl, 1 mM EDTA Reagents Disposable Plastic Material: Falcon, Eppendorf.

Media and other cell culture reagents: High Glucose DMEM and RPMI-1640: Sigma; DMEM and Ham's F12: Biowhittaker Europe; FCS: Gibco; Collagenase: Roche; L-Glutamine and Penicillin/Streptomycin solution: Biowhittaker Europe; Broths and antibiotics for bacterial cultures: LB: Sigma; TB: Gibco; Kan and Tet: Sigma; Reagents for immunohistochemistry: DAKO Cytomation.

Surgical Samples

Surgical samples are derived from surgical patients of the Institute for Cancer Research and Treatment (IRCC), Candiolo (TO), Italy, Division of Oncological Surgery. Written consensus for the participation in this study was obtained from all the donors.

For each patient one sample of normal liver and one of hepatic metastases was obtained. Samples were morphologically different for size, aspect, color, vascularization, presence of necrotic regions, and accumulation of lipid aggregates (an index of the degeneration degree induced by steatosis). The differences in the tissues are related to the different stage of progression of the disease, to the site of metastatization of the primary tumor, to other eventual causes or diseases occurred in the pathogenic process, or to other reasons related to an individual variability.

Samples were processed immediately after surgical removal, in order to disaggregate the tissues and extract single cells on which to perform the experiments. All the manipulations were performed under laminar flux in sterility. Samples were chopped with a scalpel in a small volume of PBS. The suspension, collected in PBS, was centrifuged for 3 minutes at 100 rpm at room temperature and the pellet was resuspended in 5 ml of collagenase (0.25% weight/volume in DMEM). The digestion of the tissue fragments was done incubating this suspension for 2 hours at 37° C. while shaking. The sample was again centrifuged, to eliminate all the particulate under the cell size (lipid aggregates, cell portions) or also smaller cells, of hematopoietic origin. Pellet was washed twice in PBS. Cells were filtered on filters with a diameter of 45 μm, counted in Burker chamber and resuspended at a concentration of $10^6$/ml in DMEM/FCS/HEPES.

At the microscopic examination, after tissue disaggregation and cell purification, the primary cell population appeared heterogeneous and other cell types other that hepatocytes and tumor cells could be distinguished. Among these, red blood cells, and other cells of the hematopoietic origin; fibroblasts derived from the connectival structures of the parenchyma; endothelial cells that line the blood vessels of the analyzed tissue.

Cell Lines

For the experiments of the present invention the human cell lines indicated in Table 1 were used.

Table 1

TABLE 1

| Cell line | Description |
|---|---|
| SW480 | primary colorectal cancer (ATCC CCL228) |
| SW620 | lymph node metastasis from colorectal cancer (ATCC CCL227) |
| NCI-H630 | hepatic metastasis from colorectal cancer (ATCC CRL5833) |
| HepG2 | primary hepatic cancer (ATCC HB8065) |
| AGS | primary stomach cancer (ATCC CRL1739) |
| NCI-N87 | hepatic metastasis from stomach cancer (ATCC CRL5822) |
| Capan-2 | primary pancreas cancer (ATCC HTB80) |
| Capan-1 | hepatic metastasis from pancreas cancer (ATCC HTB79) |
| BT-474 | primary breast cancer (ATCC HTB20) |
| MCF-7 | pleural effusion from breast cancer (ATCC HTB22) |
| A549 | primary lung cancer (ATCC CCL185) |
| NCI-H1688 | hepatic metastasis from lung cancer (ATCC CCI257) |

Media for Cell Culture

For the maintenance and the growth of cell lines different culture media were used, depending on cell type:

SW480, SW620, HepG2, BT-474, and MCF-7 cells were cultured in DMEM, with 10% FCS, 20 mM HEPES, L-glutamine (40 mM), Penicillin (200 U/ml), and Streptomycin (200 μg/ml).

NIC-H630, NCI-H87, NCI-H1688, Capan-1, and Capan-2 cells were cultured in RPMI-1640, with 10% FCS, L-glutamine (40 mM), Penicillin (200 U/ml), and Streptomycin (200 μg/ml).

A549 and AGS cells were cultured in Ham's F12, with 10% FCS, L-glutamine (40 mM), Penicillin (200 U/ml), and Streptomycin (200 μg/ml).

Cell Cultures

Cultures were started from cells stored in liquid nitrogen in a solution of FCS with 10% DMSO. Cells, after quick thawing at 37° C., were cultured in 100×20 mm dishes, in humidified incubator at 37° C. with 5% $CO_2$. The complete replacement of the culture medium was done every 3-4 days. When the 80-90% of confluence was reached, cells were washed in PBS and detached by incubating with a solution of 0.05% Trypsin, 2 mM EDTA at 37° C. for 3 minutes. An excess volume of medium with 10% FCS was then added and cells were collected by precipitation at 1,000 rpm for 3 minutes. Supernatant was removed, the pellet was resuspended in complete medium and aliquoted in 4 new dishes.

For the phage display experiments, cells were washed in PBS with 10 mM EDTA, and incubated in the same solution for 3 minutes at 37° C. The cell suspension was then harvested in PBS in a total volume of 10 ml. After counting in the Burker chamber, cells were resuspended in DMEM/FCS/HEPES at a final concentration of $1 \times 10^6$ ml.

Phage Libraries

For the phage display experiments, two cyclic libraries of the $CX_7C$ and $CX_3CX_3CX_3C$ types, and one linear library of the $CX_9$ type were used. In these libraries, the insert is expressed in 5 identical copies as a fusion peptide at the N-terminal of the pIII protein. The cysteine of the insert, close to the capsid surface, is covalently bound to the phage protein and, in the case of the $CX_7C$ library, can form a di-sulfide bond with the cysteine at the opposite side. As a consequence, the peptide is cyclized. In the $CX_3CX_3CX_3C$ library, instead, different combinations of di-sulfide bridges can form, which lead to multiple cyclizations and to the exposure of tri-peptide motifs.

The $CX_9$ library is linear and there is no cyclization but in a case in which the last amino acid is a cysteine as well. Phage libraries are conserved at 4° C. in TBS, at a concentration of $10^{10}$-$10^{12}$ TU/ml.

Broths and Plates for Bacterial Cultures

LB: this medium was supplemented either with Kan, to a final concentration of 20 μg/ml, for the amplification of *Escherichia coli* bacteria strain K91kan, or with both Kan and Tet, both 20 μg/ml, for bacteria amplification after the infection.

TB: this broth was used to render the K91 kan bacteria competent to infection, and was supplemented with Kan, to a final concentration of 20 μg/ml.

Plates: bacteria were amplified in Petri plates on a semi-solid substrate composed as follows: LB with 15% weight/volume bacteriological agar, and Kan (20 μg/ml) for the growth of K91 kan, or Kan (20 μg/ml) and Tet (40 μg/ml) for the growth of the infected bacteria.

Library Selection on the Cells

For all the procedures regarding phage display, protocols known in the literature were used. In particular, the protocol for the whole cell panning is derived from described methods, but it was adapted to the system in analysis, after several tests, with the aim of optimizing the application.

First round. A microliter of the library was incubated with $5 \times 10^5$ fresh metastatic cells, in a total volume of 500 μl in DMEM/FCS/HEPES, for 16 hours at 4° C., under mild shaking. Four washes in the same medium were then performed, to eliminate the weakly bound phages or the phages left in solution. The washes were performed in 1 ml of the same medium.

Successive rounds. In the successive selection rounds, 50 μl of the phages obtained from round I were incubated with $5 \times 10^5$ cells of normal liver from the same patient in 500 μl of DMEM/FCS/HEPES. This negative pre-selection step lasted 1 hour at room temperature under mild shaking, and was repeated twice. Then the supernatant was divided in two parts that were added to $5 \times 10^5$ cells of either normal liver or hepatic metastatic cells, respectively. The two cell suspensions were incubated for 2 hour at 4° C. under mild shaking. Washes as described followed. Bound phages were collected by infecting competent bacteria.

Infection of the Bacteria and Phase Amplification

Bacteria were grown in 10 ml of TB with Kan, at 37° C. while shaking for 2-3 hours, until they reached the optical density of 1.5-2.0 at the 600 nm wavelength. One milliliter of competent bacteria was then added to the 100 μl of cell suspension after washing. Infection lasted 1 hour at room temperature. At the end of the incubation, part of the bacteria were plated, in duplicate, on Petri plates with LB-agar and Tet, and incubated for 16 hours at 37° C. This system allows to grow only the phage-infected bacteria, since only the phages carry the resistance to this antibiotic. The TU related to the substrate bound phage were evaluated colony counting of each plate. Here we refer to this value with the term "Output".

The remaining part of the bacteria was added to 10 ml of LB with Tet and Kan and grown for 16 hours at 37° C. while shaking.

Phage Purification

This procedure was used to purify both phage populations deriving from selection rounds and single phage clones. The bacterial culture was centrifuged at 5,000 rpm for 10 minutes at 4° C. to eliminate the bacteria. The phages, now in the supernatant, were precipitated with 0.15 volumes of PEG/NaCl for 1 hour at 4° C. and collected by centrifugation at 6,000 rpm for 15 minutes at 4° C. After having decanted the supernatant, the pellet was compacted by further centrifuging at 6,000 rpm for 5 minutes at 4° C. and then resuspended, through shaking for 10 minutes, in 500 μl of TBS. To eliminate the debris, the suspension was then centrifuged at 12,000 rpm for 10 minutes at room temperature. The phage population was collected and stored at 4° C.

Phage Titration

The titration allows evaluating the amount of starting TU for each round or the titer of the single clones (amount to which we here refer as "Input"). To perform the titration, from the original phage suspension the dilutions described in Table 2 have been made.

TABLE 2

| sample (1) | 1 μl of the phage suspension + 99 μl of PBS ($1 \times 10^{-2}$ dilution) |
|---|---|
| sample (2) | 10 μl of sample (1) + 90 μl of PBS ($1 \times 10^{-3}$ dilution) |
| sample (3) | 10 μl of sample (2) + 90 μl of PBS ($1 \times 10^{-4}$ dilution) |
| sample (4) | 10 μl of sample (3) + 90 μl of PBS ($1 \times 10^{-5}$ dilution) |
| sample (5) | 10 μl of sample (4) + 90 μl of PBS ($1 \times 10^{-6}$ dilution) |
| sample (6) | 20 μl of sample (5) in a new tube |
| sample (7) | 2 μl of sample (6) + 18 μl of PBS ($1 \times 10^{-7}$ dilution) |
| sample (8) | 2 μl of sample (7) + 18 μl of PBS ($1 \times 10^{-8}$ dilution) |

100 μl of the samples (6), (7), and (8), that is of the $1 \times 10^{-6}$, $1 \times 10^{-7}$ and $1 \times 10^{-8}$ *dilutions*, were plated on Petri plates with agar and Tet. Plates were incubated for 16 hours at 37° C. The number of total TU was then evaluated by colony counting and referred to the total volume.

Single Clone Binding Assays

These assays were performed with an Input of $10^9$ TU of each clone, on cells from the hepatic metastasis cell line (target) and on cells from normal liver (negative control). The Output of these experiments was normalized on binding to an insertless phage, fd-tet, giving a measure of the unspecific interaction due to the phage itself. The binding increase was evaluated as ratio between normalized Output of the target and normalized Output of the negative control. All the experiments were repeated at least 3 times, when possible for material availability.

Isolation and Amplification of the Clones

When a significant increase was observed between the number of phages bound to metastatic cells compared to those bound to the normal liver cells, single clones were isolated to identify the sequence of their insert and to evaluate their binding specificity. For clone amplification, bacteria from single colonies were grown in 5 ml of LB with Kan and Tet for 16 hours at 37° C. while shaking. Phages were then purified as described.

For mechanically disaggregating the phage capsid, resin beads were used, named Strataclean Beads by the manufacturer. Before their use, the beads were resuspended in TBS in a 1:1 volume/volume ratio. For each clone, 200 μl of phage suspension was added to 10 μl of beads and vortexed for 30 seconds. After centrifugation at 400 rpm for 3 minutes, 195 μl of supernatant were collected and subjected to the same disaggregation cycle. Finally, 150 μl of supernatant were filled up to 410 μl with TE, and DNA was precipitated by incubation with 0.1 volumes of Sodium Acetate pH 5.5, and 2.2 volumes of 100% ethanol. DNA was collected by centrifugation for 10 minutes at 12,000 rpm, washed in 70% ethanol and resuspended in ultrapure $H_2O$. DNA amount was evaluated both by reading its absorbance at a 260 nm wavelength and by electrophoresis on 1% agarose gels in TAE.

Preparation of Samples for Sequencing

Ten microliters of the solution, corresponding to about 800 ng of phage DNA, were incubated with 3 pmol of the following primer: 5'-CCCTCATAGTTAGCGTAACG-3' (SEQ ID NO. 202), which corresponds to a zone immediately downstream from the oligonucleotide insert.

Sequence Analysis

To translate the nucleotide sequences into peptide sequences we used the software DNAs is V2.5.

Protocol of Immunohystochemistry with the Phages

Tissue samples were embedded in OCT and stored at −80° C. For the experiment, they were cut using a cryostate at −20° C.

Tissues were cut in 10 μm slides. These slides were then treated with PBS for 5 minutes, until OCT was completely removed. Tissues were fixed in 4% PAF in PBS for 10 minutes at room temperature, then washed for 5 minutes in PBS and incubated with 50 mM $NH_4Cl$ in PBS for 20 minutes.

Tissue peroxidases were then inactivated by treating with 3% $H_2O_2$ in $H_2O$ for 10 minutes in the dark at room temperature. One wash for 5 minutes in PBS followed.

The unspecific interaction sites were blocked by incubating the samples in the "DAKO block" reagent for 30 minutes at room temperature. Phages were then added (from $1 \times 10^6$ to $5 \times 10^6$ total TU) diluted into the "DAKO diluent" reagent; incubation lasted overnight at 4° C. After 4 washes of 5 minutes each in TBS, samples were stained with a rabbit polyclonal anti M13 phage antibody (Sigma B7786), diluted 1:500 in the "DAKO diluent" reagent, for 1 hour at room temperature.

The labeling was done using a secondary "DAKO envision" anti-rabbit antibody, developed with the AEC substrate for 5 minutes and followed by a control-staining with Mayer's hematoxylin.

GST-Fused Peptide Purification

Some of the selected peptides were produced in *Escherichia coli* as a fusion protein with GST using standard purification protocols.

Preparation and Lysis of the Bacteria:

1. inoculate the bacteria and grow overnight in 20 TB/Amp broth at 30° C.;
2. transfer bacteria in 300 ml of TB/Amp broth at 30° C.; shake for 1 hour;
3. add IPTG (final concentration 1 mM) and incubate for 2 hours;
4. centrifuge at 5,000 rpm for 15 minutes at 4° C.;
5. resuspend bacteria in 10 ml of buffer A;
6. centrifuge at 3,000 rpm for 20 minutes at 4° C.;
7. resuspend pellet in 5 ml, sonicate bacteria with four pulses of 20 seconds each at 35% power;
8. centrifuge at 11,000 rpm for 20 minutes at 4° C. and collect supernatant.

Glutathione-Agarose Resin Preparation:
9. hydrate 250 µl of resin in distilled H.sub.2O, in rotation for 1 hour;
10. wash the resin 3 times in buffer A and finally resuspend it in an equal volume of buffer A.

Purification of the Recombinant Proteins:
11. add 250 µl of resin to the sample of step 8;
12. rotate at 4° C. for 1 hour;
13. wash 3 times in buffer A;
14. evaluate the concentration by electrophoresis followed by Coomassie blue staining.

Polymerization mix for SDS-polyacrylamide gel electrophoresis (Table 3).

TABLE 3

| 12% running gel | Acrylamide/Bis-Acrylamide (4 ml) |
| --- | --- |
| | 1.5 M Tris pH 8.8 (3.75 ml) |
| | 10% SDS (0.1 ml) |
| | Bidistilled water (2.15 ml) |
| | Ammonium Persulfate (100 mg/ml) (33 µl) |
| | TEMED (8 µl) |
| 5% stacking gel | Acrylamide/Bis-Acrylamide (0.8 ml) |
| | 0.5 M Tris pH 6.8 (650 µl) |
| | 10% SDS (0.05 ml) |
| | Bidistilled water (3.55 ml) |
| | Ammonium Persulfate (100 mg/ml) (30 µl) |
| | TEMED (5 µl) |

Coomassie Blue Staining
1. incubate the gel with Coomassie Blue for 30-45 minutes in mild agitation;
2. destain in 45% methanol-10% acetic acid;
3. rehydrate in water, eventually dry on paper.

Cell Lysis

Twenty 100×20 mm dishes of HepG2 (hepatoma) or NCI-H630 (liver metastasis secondary to colorectal carcinoma) cells were mechanically detached in PBS and resuspended in 2 volumes of buffer H, with 10% glycerol and 0.1% Nonidet-P40. These suspensions were incubated for 30 minutes at 4° C. under agitation and then centrifuged at 2,500 rpm for 30 minutes at 4° C. Protein concentration was evaluated by the BCA kit (Pierce), following the instructions of the manufacturer.

Pull-Down Assay

The GST-peptides bound to the resin were incubated overnight at 4° C. with milk and washed 7 times in buffer A. 10 mg of total protein lysate were incubated with 12 µg of GST-resin at 4° C. for 1 hour twice to eliminate the proteins that bind non-specifically to GST or to the resin. The pull-down assay was performed on the unbound proteins, with 12 µg of GST-peptide-resin, overnight at 4° C.

After 4 washes in buffer A, proteins bound to the GST-peptide-resin complex were eluted in 20 mM Glutathione for 30 minutes at 4° C. and collected by centrifugation at 3,000 rpm for 2 minutes a 4° C.

The supernatant was loaded on a 10% polyacrylamide denaturing gel. This gel was then stained with a Coomassie Blue solution and the specific bands were collected and analyzed by mass spectrometry and micro-sequencing (with standard protocols).

Results

Search for Peptide Motifs Specific for Human Hepatic Metastases

To find peptides which specifically bind to human hepatic metastases, phage library screenings were performed on suspended cells derived from normal liver and metastasis samples, surgically removed from the liver of patients. In this phase, 11 couples of samples from different patients were used (patients 2, 5, 6, 7, 8, 16, 17, 18, 19, 21, 23). In almost all of the samples, the hepatic metastases were secondary to primary tumors of the colon or rectum, with the exclusion of patient 8, who had a brain hemangioma as a primary tumor (Table 4).

TABLE 4

| Patient | Sex | Age | Locus[1] | TN[2] | Marker[3] | Virus[4] | Necrosis[5] |
| --- | --- | --- | --- | --- | --- | --- | --- |
| 2 | F | 60 | Colon | T3N0 | CEA | No | 40% |
| 5 | M | 46 | Colon | T4N2 | CEA | No | 60% |
| 6 | M | 72 | Colon | T3N2 | CEA | No | 50% |
| 8 | F | 31 | Brain | | | No | |
| 7 | M | 64 | Colon | T3N1 | GICA | No | 15% |
| 16 | M | 45 | Colon | T4N2 | | No | 20% |
| 17 | M | 70 | Colon | T3N0 | | No | 80% |
| 18 | F | 62 | Colon | T4N0 | CEA, GICA | No | 60% |
| 19 | M | 76 | Colon | T3N0 | CEA | No | 50% |
| 21 | M | 59 | Retto | T3N0 | | No | <5% |
| 23 | F | 49 | Colon | | | No | 50% |

[1]site of the primary tumor;
[2]TN classification of the primary tumor;
[3]tumor markers;
[4]evidence of hepatitis B or C viruses in the liver;
[5]percent of necrosis into the metastasis.

In Table 4, the clinical parameters of the patients used for the selection are shown. For the patients 2, 6, 7 (2 experiments), 16, 17, 18, 19 and 21 the $CX_7C$ library was used; for patient 8, both the $CX_7C$ and the $CX_3CX_3CX_3C$ libraries on samples of two different metastases; for patient 23 the $CX_9$ library. For each experiment, 4 rounds of selection and amplification were performed.

Analysis of the Peptide Sequences Obtained in the Screening Experiments

In each experiment in which we observed a significant increase in the ratio of binding to the hepatic metastasis cells and the negative control (macroscopically healthy liver tissue), 20 phage clones were amplified and purified. The DNA of each clone was purified and sequenced to derive the peptide motif. Selected peptides are shown in FIG. 1.

Some sequences are particularly represented, both in a same experiment and in experiments performed on samples of different patients. In the experiments performed on patients 2, 5, 6, 7, 8, 21, and 23 peptides were selected that share common sequences, particularly tri-/tetra-peptide motifs (among which GGG, RGL, GRL, GSG, LGR, GLS, SAD, YEG, GSGS (SEQ ID NO: 208)). In the experiments performed on patients 16, 17 and 18 we found more repeated sequences. In these experiments motifs with high homology with those previously described came out as well. The most repeated peptide is LRS.

Analysis of the Selected Sequences

The attention was focused to the study of the sequences obtained in the experiments 16, 17 and 18, in particular: ARPGLRS (SEQ ID NO. 1); MRYALRS (SEQ ID NO. 2); LRPGLRS (SEQ ID NO. 3); LRSGSGS (SEQ ID NO. 4); VRSGRGS (SEQ ID NO. 5); GIYRLRS (SEQ ID NO. 6); and GVYSLRS (SEQ ID NO. 7). To identify sequence homologies among these peptides and known proteins, a search in the BLAST data bank was done. From these analyses it emerged that a significant number of peptides share sequence homologies with proteins of the extracellular matrix and with molecules of cell adhesion/motility.

Binding Experiments on Cell Lines

To evaluate if the selected inserts were specific ligands for surface determinant peculiarly expressed in the hepatic metastases, the 7 clones were tested on the cell lines described in Table 1. A summary of the results is shown in Tables 5 and 6.

In this study model, selected peptide sequences do not bind to cells derived from primary tumors (with the exception of BT-474). On the contrary, these sequences preferentially bind to cells derived from hepatic metastases (6 out of 7 clones bind to cells of hepatic metastasis secondary to primary colon tumor, 3 out of 7 clones bind to cells of hepatic metastasis secondary to primary stomach or lung tumor).

TABLE 5

| SEQ ID NO. | Hep-G2 Liver tumor | SW480 Colon tumor | SW620 Lymph node meta of colon tumor | NCI-H630 Hepatic meta of colon tumor | AGS Stomach tumor | NCI-N87 Hepatic meta of stomach tumor |
|---|---|---|---|---|---|---|
| 1 | − | − | − | − | − | − |
| 2 | − | − | + | + | − | + |
| 3 | − | − | − | + | − | − |
| 4 | − | − | − | + | − | + |
| 5 | − | − | − | + | − | + |
| 6 | − | − | − | + | − | − |
| 7 | − | + | − | − | − | − |

TABLE 6

| SEQ ID No. | Capan-2 Pancreas tumor | Capan-1 Hepatic meta from pancreas tumor | BT-474 Breast tumor | MCF-7 Pleural effusion of breast tumor | A549 Lung tumor | NCI-H1688 Hepatic meta of lung tumor |
|---|---|---|---|---|---|---|
| 1 | − | − | − | − | − | + |
| 2 | − | − | − | − | − | − |
| 3 | − | − | − | − | − | − |
| 4 | − | − | + | + | + | + |
| 5 | − | − | + | − | − | − |
| 6 | − | − | − | + | − | + |
| 7 | − | − | − | − | + | − |

Binding Experiments on Primary Cells

To evaluate if the selected inserts were specific for ubiquitous surface determinants in human hepatic metastases, the 7 selected clones were tested on primary cells of hepatic metastasis, comparing to normal liver of the same patients. For these binding assays, samples from 9 patients were used (20, 21, 22, 25, 26, 27, 28, 31, 32), with the same conditions described for the cell lines. A summary of the results is shown in Table 7.

TABLE 7

| SEQ ID NO. | P#20 | P#21 | Pz.#22 | P#25 | P#26 | P#27 | P#28 | P#31 | P#32 |
|---|---|---|---|---|---|---|---|---|---|
| 1 | + |   |   |   | + | + | + | + | + |
| 2 | + |   |   |   | + | − | − | + | + |
| 3 | + | + |   |   | + | + | + | + | + |
| 4 | − |   | + |   | + | + | + | + | + |
| 5 |   |   | − |   | + | + | + | + | + |
| 6 |   |   |   | + | + | + | + | + | + |
| 7 |   | + | + |   | + | + | + | + | + |

In the first experiments, due to the low cell numbers, related to the set up phase of the purification procedure, the binding of only some clones was evaluated. In general, 3 assays have been performed for each sample. From all these experiments it emerges that the less functional clone as universal diagnostic marker is the one that displays the MRY-ALRS sequence (SEQ ID NO. 2), which gave negative results in two assays (27, 28), while the clones that worked on all the samples are those exposing the sequences ARPGLRS (SEQ ID NO. 1), LRPGLRS (SEQ ID NO. 3), GIYRLRS (SEQ ID NO. 6), and GVYSLRS (SEQ ID NO. 7). It is interesting to note that, in the experiments on fresh cells, binding increases are much higher than in those performed with the cultured cell lines.

Binding Overlay Experiments on Tissue Samples

Binding overlay assays with phages having the sequences GIYRLRS (SEQ ID NO. 6), and GVYSLRS (SEQ ID NO. 7) were performed on 64 tissue samples (tumor and metastasis tissues from 37 different patients): 18 samples of hepatic metastasis and cognate healthy tissue; 4 samples of primary colon tumor; 2 samples of primary rectum tumor; 2 samples of healthy colon; 3 samples of primary breast tumor; 6 samples of primary ovary tumor with cognate omental metastases (one with sigma metastasis); 2 lung metastases secondary to colorectal tumors and 2 lung metastases secondary to renal tumor. The results of all the assays is shown in Table 8.

TABLE 8

| Tissue type | Result | % positive samples |
|---|---|---|
| hepatic meta secondary to colorectal tumor | +++ | 75 |
| healthy colon | − | 0 |
| healthy liver | − | 0 |
| primary colorectal tumor | − | 0 |
| primary ovary tumor | −+ | 10 |
| omental meta of ovary tumor | −+ | 10 |
| sigma meta of ovary tumor | − | 0 |
| lung meta of colorectal tumor | − | 0 |
| lung meta of renal tumor | − | 0 |

Receptor Purification

The search for molecules specifically present on the surfaces of the metastatic cells was performed by pull-down experiments, using NCI-H630 (as a substrate, being positive to the binding of 6 out of 7 phages) and HepG2 (as a control, being negative to the binding of all the phages). The pull-down was performed using the peptide GIYRLRS (SEQ ID NO. 6), present as a fusion with the GST protein. This experiment was repeated three times. In FIG. 3 a denaturing polyacrylamide gel is shown, in which the GIYRLRS-GST-bound proteins (SEQ ID NO: 6) have been separated and stained with Coomassie Blue. In the figure: MM, molecular weight markers, HepG2, lysate of the HepG2 cells; NCI-H630, lysate of the NCI-H630 cells; numbers 250, 150, 100, 75, 50, 37, 25 indicate the standard molecular weights; numbers from 1 to 9 indicate the bands analyzed. Proteins were identified by mass spectrometry.

Obviously, the details of the realization and the embodiments can be largely varied compared to what is here described and illustrated, without exiting from the field of the present invention, as defined by the claims included.

BIBLIOGRAPHY

1. Arap, W., Pasqualini, R. & Ruoslahti, E. Chemotherapy targeted to tumor vasculature. Curr. Opin. Oncol. 10, 560-565 (1998).
2. Pasqualini, R., Arap, W., Rajotte, D. & Ruoslahti, E. in Phage display: a laboratory manual (eds. Barbas, C. F., Burton, D. R., Scott, J. K. & Silverman, G. J.) 1-24 (Cold Spring Harbor Laboratory Press, Cold Spring Harbor, N.Y., 2000).
3. Del Gatto, A. et al. Novel and selective alpha(v) beta3 receptor peptide antagonist: design, synthesis, and biological behavior. J Med Chem 49, 3416-20 (2006).
4. Colombo, G. et al. Structure-activity relationships of linear and cyclic peptides containing the NGR tumor-homing motif. J Biol Chem 277, 47891-7 (2002).
5. Corti, A. & Ponzoni, M. Tumor vascular targeting with tumor necrosis factor alpha and chemotherapeutic drugs. Ann N Y Acad Sci 1028, 104-12 (2004).
6. Curnis, F. et al. Differential binding of drugs containing the NGR motif to CD13 isoforms in tumor vessels, epithelia, and myeloid cells. Cancer Res 62, 867-74 (2002).
7. Di Matteo, P. et al. Immunogenic and structural properties of the Asn-Gly-Arg (NGR) tumor neovasculature-homing motif. Mol Immunol 43, 1509-18 (2006).
8. Koivunen, E., Wang, B. & Ruoslahti, E. Isolation of a highly specific ligand for the alpha 5 beta 1 integrin from a phage display library. J Cell Biol 124, 373-80 (1994).
9. Pasqualini, R. et al. Aminopeptidase N is a receptor for tumor-homing peptides and a target for inhibiting angiogenesis. Cancer Res 60, 722-7 (2000).
10. Pastorino, F. et al. Vascular damage and anti-angiogenic effects of tumor vessel-targeted liposomal chemotherapy. Cancer Res 63, 7400-9 (2003).
11. Burg, M. A., Pasqualini, R., Arap, W., Ruoslahti, E. & Stallcup, W. B. NG2 proteoglycan-binding peptides target tumor neovasculature. Cancer Res. 59, 2869-2874 (1999).
12. Koivunen, E. et al. Tumor targeting with a selective gelatinase inhibitor. Nat. Biotechnol. 17, 768-774 (1999).
13. Ellerby, H. M. et al. Anti-cancer activity of targeted pro-apoptotic peptides. Nat. Med. 5, 1032-1038 (1999).
14. Scott, J. K. & Smith, G. P. Searching for peptide ligands with an epitope library. Science 249, 386-390 (1990).
15. Smith, G. P. & Scott, J. K. Libraries of peptides and proteins displayed on filamentous phage. Methods Enzymol. 217, 228-257 (1993).

The invention claimed is:

1. A peptide capable of selectively binding to metastatic cells having the sequence motif LRS, a length of 6 to 100 amino acids and comprising an amino acid sequence selected from the group consisting of: ARPGLRS (SEQ ID NO. 1), MRYALRS (SEQ ID NO. 2), LRPGLRS (SEQ ID NO. 3), GIYRLRS (SEQ ID NO. 6), GVYSLRS (SEQ ID NO. 7), SWYTLRS (SEQ ID NO. 111), LAYRLRS (SEQ ID NO. 113), LTYRLRS (SEQ ID NO. 115), and VRPGLRS (SEQ ID NO. 117).

2. A peptide of claim 1, wherein said metastatic cells are human hepatic metastasis cells.

3. A peptide of claim 1 A peptide capable of selectively binding to metastatic cells having the sequence motif LRS, a length of 6 to 100 amino acids and comprising an amino acid sequence selected from the group consisting of: ARPGLRS (SEQ ID NO. 1), MRYALRS (SEQ ID NO. 2), LRPGLRS (SEQ ID NO. 3), GIYRLRS (SEQ ID NO. 6), GVYSLRS (SEQ ID NO. 7), SWYTLRS (SEQ ID NO. 111), LAYRLRS (SEQ ID NO. 113), LTYRLRS (SEQ ID NO. 115), and VRPGLRS (SEQ ID NO. 117), which is a cyclic peptide.

4. A conjugate comprising at least a peptide according to claim 1 capable of selectively binding to metastatic cells having the sequence motif LRS, a length of 6 to 100 amino acids and comprising an amino acid sequence selected from the group consisting of: ARPGLRS (SEQ ID NO. 1), MRYALRS (SEQ ID NO. 2), LRPGLRS (SEQ ID NO. 3), GIYRLRS (SEQ ID NO. 6), GVYSLRS (SEQ ID NO. 7), SWYTLRS (SEQ ID NO. 111), LAYRLRS (SEQ ID NO. 113), LTYRLRS (SEQ ID NO. 115), and VRPGLRS (SEQ ID NO. 117), and at least one molecule.

5. A conjugate of claim 4, wherein said at least one molecule is selected among a drug, a chemotherapic agent, a radioisotope, a pro-apoptotic agent, an anti-angiogenic agent, an hormone, a cytokine, a cytotoxic agent, a cytostatic agent, a peptide, a protein, an antibody, an antibody fragment and a Fab fragment.

6. A conjugate of claim 5, wherein said anti-angiogenic agent is selected from the group consisting of thrombospondin, angiostatin, pigment epithelium-derived factor, angiotensin, laminin peptides, fibronectin peptides, plasminogen activator inhibitors, tissue metalloproteinase inhibitors, interferons, interleukin 12 (IL-12), platelet factor 4, IP-10, 2-methoxyoestradiol, proliferin-related protein, carboxiamidotriazole, CM101, Marimastat, pentosan polysulphate, angiopoietin 2, interferon-alpha, herbimycin A, PNU145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline.

7. A conjugate of claim 5, wherein said pro-apoptotic agent is selected from the group consisting of etoposide, ceramide sphingomyelin, Bax, Bid, Bik, Bad, caspase-3, caspase-8, caspase-9, fas, fas ligand, fadd, fap-1, tradd, faf, rip, reaper, apoptin, interleukin-2 converting enzyme and annexin V.

8. A conjugate of claim 5, wherein said cytokine is selected from the group consisting of interleukin 1 (IL-1), IL-2, IL-5, IL-10, IL-11, IL-12, IL-18, interferon-gamma (IF-gamma), IF-alpha, IF-beta, tumor necrosis factor-alpha (TNF-alpha), and GM-CSF (granulocyte macrophage colony stimulating factor).

9. A conjugate of claim 4, wherein said at least one molecule is selected from a virus, a bacteriophage, a bacterium, a liposome, a microparticle, a magnetic bead, a nanoparticle, a yeast cell, and a mammalian cell.

10. A conjugate of claim 9, wherein said virus is selected from an adenovirus, a retrovirus, an adeno-associated virus, and a lentivirus.

11. A conjugate of claim 4, wherein said at least one molecule is a diagnostic agent.

12. A conjugate of claim 11, wherein said diagnostic agent is a diagnostic agent for in vivo use.

13. A conjugate of claim 12, wherein said diagnostic agent is selected from paramagnetic ions or radioisotopes.

14. A conjugate of claim 11, wherein said diagnostic agent is a diagnostic agent for in vitro assays.

15. A formulation comprising at least one peptide of claim 1 capable of specifically binding to metastatic cells.

16. A formulation of claim 15, wherein said at least one peptide is conjugated with a drug.

17. A formulation of claim 16, comprising at least one peptide capable of selectively binding to metastatic cells having the sequence motif LRS, a length of 6 to 100 amino acids and comprising an amino acid sequence selected from the group consisting of: ARPGLRS (SEQ ID NO. 1), MRYALRS (SEQ ID NO. 2), LRPGLRS (SEQ ID NO. 3), GIYRLRS (SEQ ID NO. 6), GVYSLRS (SEQ ID NO. 7), LRSGRGS (SEQ ID NO. 96), RREGLRS (SEQ ID NO. 110), SWYTLRS (SEQ ID NO. 111), LAYRLRS (SEQ ID NO. 113), LTYRLRS (SEQ ID NO. 115), and VRPGLRS (SEQ ID NO. 117), wherein said peptide is conjugated with a drug, and wherein said drug is a therapeutic agent capable of having a cytotoxic, cytostatic, pro-apoptotic, or anti-angiogenic effect on hepatic metastasis cells.

18. A formulation of claim 16, wherein said drug is an alkylating agent, an anti-metabolite, or an antibiotic.

19. A formulation of claim 16, wherein said at least one peptide is conjugated with a diagnostic agent.

20. A formulation of claim 19, wherein said diagnostic agent is a diagnostic agent for in vivo use.

21. A formulation of claim 19, wherein said diagnostic agent is a diagnostic agent for in vitro assays.

22. A formulation of claims 15, which is a pharmaceutical formulation.

23. A formulation of claim 15, which includes at least one acceptable carrier and/or excipient.

24. A method for diagnosing the localization of metastatic cells in a subject with a tumor, comprising administering a peptide according to claim 1 in a formulation to said subject or to a sample from said subject.

25. The method according to claim 24, wherein said metastatic cells are hepatic metastasis cells.

26. The method according to claim 24, wherein said formulation is for in vivo use.

27. The method according to claim 24, wherein said formulation is for in vitro assays.

28. A method for anti-tumor therapy in a tumor-bearing subject, comprising administering a peptide of claim 1 to said tumor-bearing subject.

29. A process for obtaining a peptide capable of selectively binding to a metastatic cell, which has a sequence motif LRS and which has a length of 6 to 100 amino acids, whereby the process comprises (1) contacting the metastatic cell or a tissue containing metastatic cells with a plurality of phages, where each phage presents heterologous peptide sequences incorporated into a capsid protein, (2) removing phages that do not bind to the cells or tissues, (3) isolating the phages that bind the cell or tissue, and optionally (4) identifying the heterologous peptide sequences, wherein said peptide comprises at least one sequence selected from the group consisting of: ARPGLRS (SEQ ID NO. 1), MRYALRS (SEQ ID NO. 2), LRPGLRS (SEQ ID NO. 3), LRSGSGS (SEQ ID NO. 4), GIYRLRS (SEQ ID NO. 6), GVYSLRS (SEQ ID NO. 7), LRSGRGS (SEQ ID NO. 96), RREGLRS (SEQ ID NO. 110), SWYTLRS (SEQ ID NO. 111), LAYRLRS (SEQ ID NO. 113), LTYRLRS (SEQ ID NO. 115), VRPGLRS (SEQ ID NO. 117), and LRSGRGS (SEQ ID NO. 119).

30. A process of claim 29, wherein said metastatic cells are hepatic metastatic cells.

31. A process of claim 30, wherein said hepatic metastatic cells are derived from a primary colorectal tumor.

32. The method according to claim 24, wherein said subject has a colon tumor.

* * * * *